US012758333B2

(12) United States Patent
Ayvali et al.

(10) Patent No.: US 12,758,333 B2
(45) Date of Patent: Oct. 13, 2026

(54) AI-ASSISTED WORKFLOW SEGMENTATION

(71) Applicant: AURIS HEALTH, INC., Santa Clara, CA (US)

(72) Inventors: Elif Ayvali, Redwood City, CA (US); Hedyeh Rafii-Tari, Mountain View, CA (US)

(73) Assignee: Auris Health, Inc., Santa Clara, CA (US)

( * ) Notice: Subject to any disclaimer, the term of this patent is extended or adjusted under 35 U.S.C. 154(b) by 356 days.

(21) Appl. No.: 17/994,304

(22) Filed: Nov. 26, 2022

(65) Prior Publication Data

US 2023/0093555 A1 Mar. 23, 2023

Related U.S. Application Data

(63) Continuation of application No. PCT/IB2021/060591, filed on Nov. 16, 2021.

(Continued)

(51) Int. Cl.

*A61B 34/32* (2016.01)
*A61B 34/00* (2016.01)

(Continued)

(52) U.S. Cl.

CPC .............. *A61B 34/32* (2016.02); *A61B 34/20* (2016.02); *A61B 34/25* (2016.02);

(Continued)

(58) Field of Classification Search

CPC ......... A61B 34/32; A61B 34/20; A61B 34/25; A61B 2034/2057; A61B 2034/2065;

(Continued)

(56) References Cited

U.S. PATENT DOCUMENTS 6,322,567 B1 11/2001 Mittelstadt et al.
10,863,883 B2 12/2020 Iida et al.

(Continued)

FOREIGN PATENT DOCUMENTS

CN 205072959 U 3/2016
CN 106455941 A 2/2017

(Continued)

OTHER PUBLICATIONS

International Search Report for appl. No. PCT/IB2021/060591, dated Feb. 23, 2022, 4 pages.

(Continued)

*Primary Examiner* — Niketa Patel
*Assistant Examiner* — Sebastian X Lukjan
(74) *Attorney, Agent, or Firm* — Paradice & Li LLP

(57) ABSTRACT

A robotic system is configured to automatically identify phases of a medical procedure. The robotic system includes a video capture device, a robotic manipulator, one or more sensors, an input device, and control circuitry. The control circuitry is configured to: determine a first position of the robotic manipulator based on sensor data; determine a first procedure from a set of procedures based on a user input and the sensor data; narrow a set of procedure phases to a subset of the procedure phases based on the determined first procedure; perform a first analysis of a captured video of a patient site; identify a first phase of the medical procedure from the subset of the procedure phases based on the first position of the robotic manipulator and the first analysis of the video; and generate a first video marker indicating a beginning of the first phase of the medical procedure.

20 Claims, 11 Drawing Sheets

Related U.S. Application Data

(60) Provisional application No. 63/132,850, filed on Dec. 31, 2020, provisional application No. 63/116,798, filed on Nov. 20, 2020.

(51) Int. Cl.
*A61B 34/20* (2016.01)
*A61B 34/30* (2016.01)

(52) U.S. Cl.
CPC ................. *A61B 2034/2057* (2016.02); *A61B 2034/2065* (2016.02); *A61B 2034/254* (2016.02); *A61B 2034/301* (2016.02)

(58) Field of Classification Search
CPC ...... A61B 2034/254; A61B 2034/2051; A61B 2034/301; A61B 1/000094; A61B 90/361; A61B 90/98; G16H 50/20; G16H 50/70; G16H 20/40; G16H 30/40; G16H 40/63; G16H 40/67
See application file for complete search history.

(56) References Cited

U.S. PATENT DOCUMENTS

| | | | | |
|---|---|---|---|---|
| 10,864,050 | B2 * | 12/2020 | Tabandeh | A61B 34/20 |
| 10,977,495 | B2 * | 4/2021 | Hares | G06V 20/20 |
| 11,172,950 | B2 | 11/2021 | Cheon et al. | |
| 12,150,723 | B2 | 11/2024 | Ayvali et al. | |
| 2004/0152970 | A1 | 8/2004 | Hunter et al. | |
| 2011/0046476 | A1 | 2/2011 | Cinquin et al. | |
| 2014/0012793 | A1 | 1/2014 | Park et al. | |
| 2014/0132928 | A1 | 5/2014 | Ono | |
| 2015/0057675 | A1 | 2/2015 | Akeel et al. | |
| 2017/0303941 | A1 * | 10/2017 | Eisner | A61M 25/09 |
| 2018/0250075 | A1 * | 9/2018 | Cho | B25J 9/161 |
| 2019/0021906 | A1 | 1/2019 | Claus | |
| 2019/0110856 | A1 | 4/2019 | Barral et al. | |
| 2019/0201140 | A1 * | 7/2019 | Yates | A61B 34/25 |
| 2019/0223961 | A1 * | 7/2019 | Barral | G16H 30/20 |
| 2020/0100855 | A1 | 4/2020 | Leparmentier et al. | |
| 2020/0110936 | A1 | 4/2020 | Hares et al. | |
| 2020/0170710 | A1 * | 6/2020 | Rus | G16H 20/40 |
| 2020/0198147 | A1 | 6/2020 | Fredrickson et al. | |
| 2020/0237452 | A1 | 7/2020 | Wolf et al. | |
| 2020/0335208 | A1 | 10/2020 | Talmor et al. | |
| 2021/0085410 | A1 | 3/2021 | Hassan | |
| 2021/0186615 | A1 * | 6/2021 | Shmayahu | B25J 9/1676 |
| 2021/0378740 | A1 | 12/2021 | Chu et al. | |
| 2022/0061868 | A1 | 3/2022 | Cheon et al. | |
| 2022/0287786 | A1 | 9/2022 | Zhan et al. | |
| 2023/0080060 | A1 | 3/2023 | Ayvali et al. | |
| 2023/0082310 | A1 | 3/2023 | Ayvali et al. | |
| 2024/0016543 | A1 | 1/2024 | Altshuler et al. | |

FOREIGN PATENT DOCUMENTS

| | | | | |
|---|---|---|---|---|
| CN | 108601623 | A | 9/2018 | |
| CN | 109806004 | A | 5/2019 | |
| JP | 2007007041 | A | 1/2007 | |
| JP | 2010234664 | A | 10/2010 | |
| JP | 2012128223 | A | 7/2012 | |
| JP | 2015160278 | A | 9/2015 | |
| JP | 2016034412 | A | 3/2016 | |
| JP | 6382381 | B1 | 8/2018 | |
| JP | 2018-538037 | A | 12/2018 | |
| KR | 101795720 | B1 | 11/2017 | |
| KR | 20180008573 | A | 1/2018 | |
| KR | 1020200096155 | A | 8/2020 | |
| WO | 2015171289 | A1 | 11/2015 | |
| WO | 2016187002 | A1 | 11/2016 | |
| WO | 2017083768 | A1 | 5/2017 | |
| WO | 2017132365 | A1 | 8/2017 | |
| WO | 2019130100 | A1 | 7/2019 | |
| WO | 2019199125 | A1 | 10/2019 | |
| WO | 2019226182 | A1 | 11/2019 | |
| WO | 2020172414 | A1 | 8/2020 | |
| WO | WO-2021155319 | A1 * | 8/2021 | A61B 34/37 |

OTHER PUBLICATIONS

Nara, A. et al., Surgical Phase Recognition Using Movement Data from Video Imagery and Location Sensor Data, Advances in Decomputation, Part of the Advances in Geographic Information Science book series (AGIS), 2017, 7 pages.
Tran, Dinh Tuan et al., Phase Segmentation Methods for an Automatic Surgical Workflow Analysis, International Journal of Biomedical Imaging, 2017, vol. 2017, article IDS 1985796, 17 pages.
Written Opinion for appl. No. PCT/IB2021/060591, dated Feb. 23, 2022, 3 pages.
International Search Report for Appl. No. PCT/IB2023/058156, dated Nov. 21, 2023, 3 pages.
Written Opinion of the International Search Authority for Appl. No. PCT/IB2023/058156, dated Nov. 21, 2023, 7 pages.
Notice of Allowance for U.S. Appl. No. 17/994,306, dated Jul. 22, 2024, 9 pages.
Bardram, J. E. et al., "Phase Recognition during Surgical Procedures using Embedded and Body-worn Sensors", 2011 IEEE International Conference on Pervasive Computing and Communications (PerCom), Seattle, WA, USA, Mar. 21-25, 2011, 9 pages.
International Search Report for appl. No. PCT/IB2021/060596, dated Feb. 15, 2022, 4 pages.
Khalid, S. et al., "Evaluation of Deep Learning Models for Identifying Surgical Actions and Measuring Performance". JAMA Network Open, Mar. 30, 2020, vol. 3, No. 3, Article No. e201664, 10 pages.
Search Report for appl No. PCT/IB2021/060592, dated Feb. 25, 2022, 4 pages.
Written Opinion for appl No. PCT/IB2021/060592, dated Feb. 25, 2022, 4 pages.
Written Opinion for appl. No. PCT/UB2021/060596, dated Feb. 15, 2022, 3 pages.
Supplementary European Search Report for Application No. 21894145.8, dated Oct. 28, 2024, 12-pages.
Notice of Allowance from U.S. Appl. No. 17/994,306, dated Jul. 22, 2024, 58 pages.
European Supplementary Search Report from EP Patent Application No. 21894144.1, dated Sep. 26, 2024, 12 pages.
Volkov et al. "Machine Learning and Coresets for Automated Real-Time Video Segmentation of Laparoscopic and Robot-Assisted Surgery," 2017 IEEE International Conference on Robotics and Automation (ICRA), IEEE, 2017, pp. 1-6.
Office Action from Japan Patent Application No. 2023-530629, dated Apr. 22, 2025, 5 pages.
Office Action from Japan Patent Application No. 2023-530631, dated Apr. 22, 2025, 14 pages.
Office Action from Japan Patent Application No. 2023-530635, dated Apr. 22, 2025, 5 pages.
Non-Final Office Action from U.S. Appl. No. 17/994,305, dated May 8, 2025, 10 pages.
Final Office Action from U.S. Appl. No. 17/994,305, dated Aug. 13, 2025, 11 pages.
Decision to Grant a Patent from Japan Patent Application No. 2023-530631, dated Mar. 31, 2026.
Decision to Grant from Japan Patent Application No. 2023-530635, dated Aug. 5, 2025, 4 pages.
Decision to Grant from Japan Patent Application No. 2023-530629 dated Sep. 30, 2025, 4 pages.
Office Action with Search Report from China Patent Application No. 202180077709.X dated Mar. 27, 2026, 22 pages.
Office Action with Search Report from China Patent Application No. 202180078079.8 dated Apr. 4, 2026, 20 pages.
Office Action, dated Oct. 7, 2025, from Japan Patent Application No. 2023-530631, 10 pages.
Non-Final Office Action from U.S. Appl. No. 17/994,305, dated Dec. 2, 2025, 12 pages.

(56) References Cited

OTHER PUBLICATIONS

Final Office Action from U.S. Appl. No. 17/994,305, dated Jun. 15, 2026, 15 pages.
Office Action from Korean Patent Application No. 10-2023-7020377, dated Jun. 9, 2026, 14 pages.
Office Action from Korean Patent Application No. 10-2023-7020383, dated Jun. 4, 2026, 18 pages.
Office Action from Korean Patent Application No. 10-2023-7020597, dated Jun. 4, 2026, 14 pages.
Office Action with Search Report from China Patent Application No. 202180077710.2 dated May 28, 2026, 22 pages. (includes English Translation).
Office Action with Search Report from China Patent Application No. 202180077709.X dated Jul. 11, 2026, 24 pages.

* cited by examiner

AI-ASSISTED WORKFLOW SEGMENTATION

CROSS-REFERENCE TO RELATED APPLICATIONS

This application is a continuation of International Application No. PCT/IB2021/060591, filed on Nov. 16, 2021 and entitled AI-ASSISTED WORKFLOW SEGMENTATION, which claims the benefit of priority to U.S. Provisional Application No. 63/116,798, filed Nov. 20, 2020, and U.S. Application No. 63/132,850, filed Dec. 31, 2020, each of which is hereby incorporated by reference in its entirety.

BACKGROUND

Field

The present disclosure relates to the field of medical devices and procedures and artificial intelligence assisted data processing.

Description of the Related Art

Various medical procedures involve the use of a robotic system that assists with using one or more medical instruments configured to penetrate the human anatomy to reach a treatment site. Certain operational processes can involve inserting the one or more medical instruments through the skin or an orifice of a patient to reach the treatment site and extract an object from the patient, such as a urinary stone.

SUMMARY

Described herein are one or more systems, devices, and/or methods to assist a physician or other medical professional in controlling a medical instrument to access an object, such as a urinary stone, located within the human anatomy.

For purposes of summarizing the disclosure, certain aspects, advantages, and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a robotic system for automatically identifying phases of a medical procedure. The robotic system also includes a video capture device; a robotic manipulator; one or more sensors for determining a configuration of the robotic manipulator; an input device configured to receive one or more user interactions and initiate one or more actions by the robotic manipulator; and control circuitry communicatively coupled to the input device and robotic manipulator. The control circuitry is configured to: determine a first position of the robotic manipulator based on sensor data from the one or more sensors; determine a first procedure from a set of procedures based on at least one of a user input and the sensor data from the one or more sensors; narrow a set of procedure phases to a subset of the procedure phases based on the determination of the first procedure; perform a first analysis of a video of a patient site captured by the video capture device; identify a first phase of the medical procedure from the subset of the procedure phases based at least in part on the first position of the robotic manipulator and the first analysis of the video; and generate a first video marker indicating a beginning of the first phase of the medical procedure. Other embodiments of this aspect include corresponding computer systems, apparatus, and computer programs recorded on one or more computer storage devices, each configured to perform the actions of the methods.

Implementations may include one or more of the following features. The set of procedures performed by the robotic system may include at least, ureteroscopy, percutaneous nephrolithotomy (PCNL) and mini-PCNL. The sensor data for determining the first procedure from the one or more sensors may include radio-frequency identification (RFID) data of one or more medical instruments utilized by the robotic manipulator. The first procedure is determined based on the user input, the user input may include at least a selection of a first UI screen associated with the first procedure. The control circuitry of the robotic system can be further configured to: determine a second position of the robotic manipulator; perform a second analysis of the video captured by the video capture device; and generate a second video marker for the video indicating an ending of a first phase of the medical procedure based at least in part on the second position of the robotic manipulator and the second analysis of the video. The robotic manipulator is configured to manipulate a medical instrument that may include a ureteroscope. The first phase may include a lasing phase, a second phase may include a basketing phase, and a third phase may include a percutaneous access phase, with the second phase and the third phase indicated by additional video markers for the video. The control circuitry of the robotic system can be further configured to: in response to identifying the beginning of the first phase, trigger automated movement of the robotic manipulator to a second position. The automated movement of the robotic manipulator to the second position may include: moving a medical instrument to an insertion site of a patient; and aligning the medical instrument along a pre-determined insertion trajectory into the insertion site. The control circuitry of the robotic system can be further configured to: in response to movement of the medical instrument by the robotic manipulator, determine whether the medical instrument is at a target location; and in response to the medical instrument reaching the target location, indicate success of the first phase on a user interface of the robotic system. The control circuitry of the robotic system can be further configured to: aggregate data on successes and failures of the first phase over multiple medical procedures; and determine a success rate for the first phase. The control circuitry of the robotic system can be further configured to: associate results of the first phase with a medical professional operating the robotic system. The robotic system may include: a sensor for determining a location of a medical instrument manipulated by the robotic manipulator. Implementations of the described techniques may include hardware, a method or process, or computer software on a computer-accessible medium.

One general aspect includes a method for automatically identifying phases of a medical procedure using a robotic system that may include a video capture device. The method also includes determining a first position of the robotic manipulator based on sensor data from the one or more sensors; determining a first procedure from a set of procedures based on at least one of a user input and the sensor data from the one or more sensors, narrowing a set of procedure phases to a subset of the procedure phases based on the determination of the first procedure, performing a first analysis of a video of a patient site captured by the video capture device, identifying a first phase of the medical procedure from the subset of the procedure phases based at least in part on the first position of the robotic manipulator and the first analysis of the video, and generating a first video marker indicating a beginning of the first phase of the medical procedure. Other embodiments of this aspect include corresponding computer systems, apparatus, and computer programs recorded on one or more computer storage devices, each configured to perform the actions of the methods.

Implementations may include one or more of the following features. The method may include: determining a second position of the robotic manipulator; performing a second analysis of the video; and generating a second video marker for the video indicating an ending of a first phase of the medical procedure based at least in part on the second position of the robotic manipulator and the second analysis of the video. In some implementations, the first procedure is ureteroscopy and the first phase may include a surveying phase, a second phase may include a lasing phase, and a third phase may include a basketing phase. The method may include: generating markers indicating the second phase and the third phase based at least in part on positions of the robotic manipulator, analysis of the video, and user input from the input device. The method may include: in response to identifying the beginning of the first phase, triggering automated movement of the robotic manipulator to a second position. The automated movement of the robotic manipulator to the second position may include: moving a medical instrument to an insertion site of a patient; and aligning the medical instrument along a pre-determined insertion. The method may include: in response to movement of the medical instrument by the robotic manipulator, determining whether the medical instrument is at a target location; and in response to the medical instrument reaching the target location, indicating success of the first phase on a user interface of the robotic system. The method may include: aggregating data on successes and failures of the first phase over multiple medical procedures; and determining a success rate for the first phase. Implementations of the described techniques may include hardware, a method or process, or computer software on a computer-accessible medium.

One general aspect includes a control system for automatically identifying phases of a medical procedure performed by a robotic device. The control system also includes a communication interface configured to receive sensor data, user input data, and video data from the robotic device; memory configured to store the sensor data, the user input data, and the video data; and one or more processors configured to: determine a first position of the robotic device from the sensor data; determine a first procedure from a set of procedures based on at least one of a user input and the sensor data from the one or more sensors; narrow a set of identifiable procedure phases to a subset of the procedure phases based on the determination of the first procedure; perform a first analysis of a video of a patient site captured by the video capture device; identify a first phase of the medical procedure from the subset of the procedure phases based at least in part on the first position of the robotic device and the first analysis of the video; and generate a first video marker indicating a beginning of the first phase of the medical procedure. Other embodiments of this aspect include corresponding computer systems, apparatus, and computer programs recorded on one or more computer storage devices, each configured to perform the actions of the methods.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
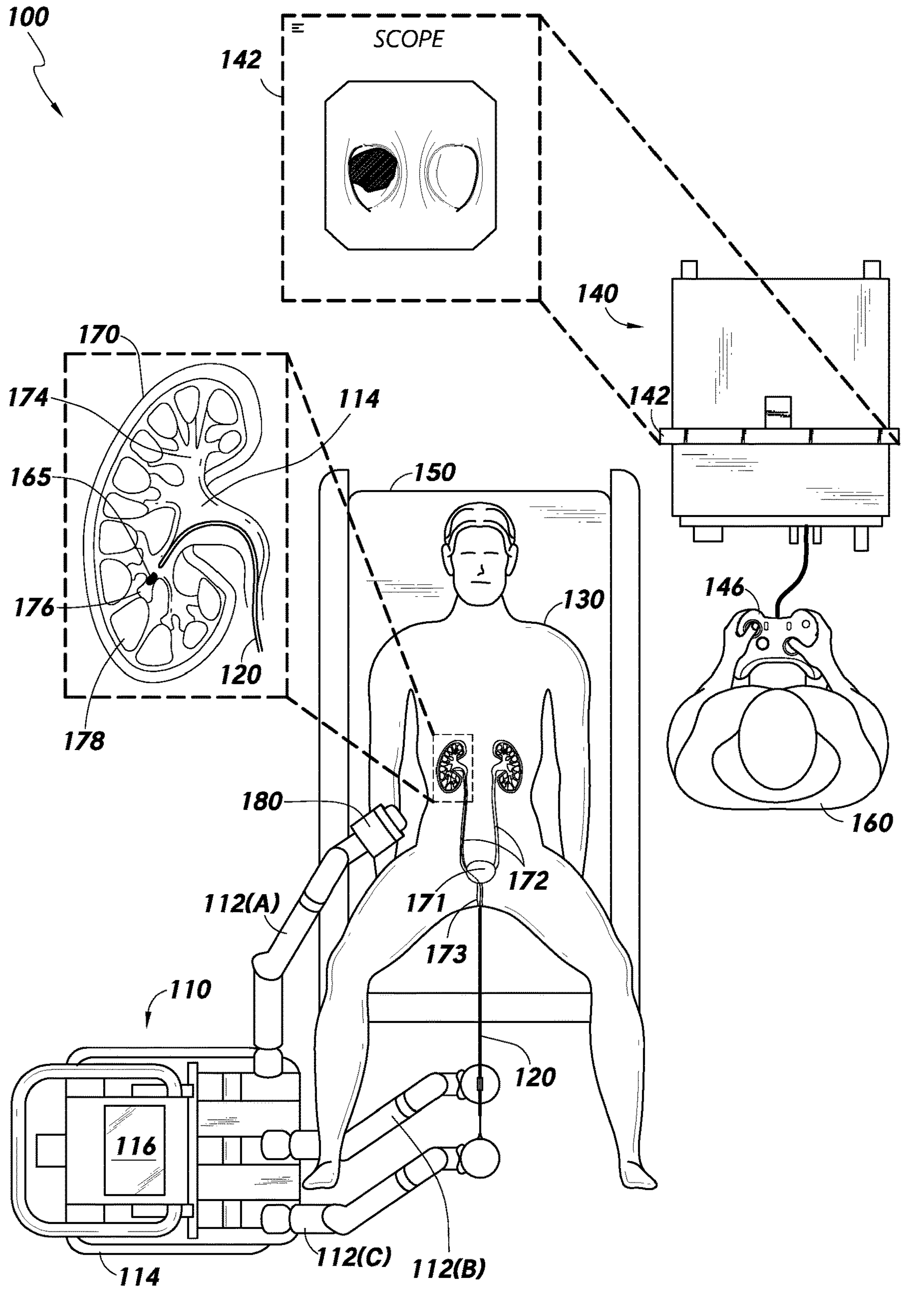
FIG. 1 illustrates an example medical system to perform or assist in performing medical procedures, according to certain embodiments.

The headings provided herein are for convenience only and do not necessarily affect the scope or meaning of disclosure. Although certain preferred embodiments and examples are disclosed below, the subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location may be used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to techniques and systems for collecting and analyzing data from robotic assisted medical procedures, such as those performed by a robotic system for stone management (e.g., retrieving urinary stones, suction of stone fragments, etc.) or performing other medical procedures. A medical procedure may progress through several different phases. For example, in ureteroscopy, phases can include percutaneous insertion of a medical instrument into the body, travel to the urinary stone location, lasing of the urinary stone, and/or basketing of the broken up stone. Robotic systems typically have several sensors and input devices, allowing the generation of a large amount of data during the medical procedure. This procedure data can be used to automatically determine the different phases of the operation. By identifying these phases, the robotic system can anticipate and prepare for the actions of the medical professional operating the robotic system during the medical procedure.

A medical system comprising the robotic system may also allow annotating of video footage of the procedure with metadata identifying the different phases. This allows the video footage to be more easily reviewed by users as well as allowing for more sophisticated analysis of the video footage using artificial intelligence (AI). This can make it easier to evaluate and score the actions performed by the user or operator by comparing those actions to similar actions from corresponding phases performed during other procedures. For example, the video footage and associated data can be analyzed by AI systems to generate statistics for the operation, such as attempts before success per phase or entire procedure, time of each phase, number of articulation commands provided by the operator, accuracy of the needle insertion, and/or the like. Furthermore, data can be aggregated over several operations and used to generate statistics for the type of operation in general, such as success rates, average operation times per phase or entire procedures, and/or the like. Such a medical system can also provide additional benefits, such as by generating case summaries.

In one example scenario, there are distinct phases during percutaneous renal access or other procedures. In an exemplary workflow, the user drives the scope to a desired calyx, marks the papilla and retracts the scope to see the target papilla. The user then holds the needle, selects an insertion site, and aligns the needle trajectory with the target papilla using a graphical user interface ("GUI"). Finally, the user inserts the needle while following the graphical user interface to gain access to the kidney through the target papilla. To improve procedure efficiency and assess user skill, the medical system can label the beginning and end of these events and obtain ground truth data on whether the percutaneous access ("perc") attempt was successful or not.

After dividing the case data into distinct phases and generating a phase transition chart showing these phases, the transition chart can be used to evaluate the procedure. For example, one example transition chart may show that the physician selected a target and an insertion site, but did not move forward with needle alignment step, and instead drove to a different calyx to select a new target. The chart may show that the physician did not get a visual confirmation of access in the first percutaneous access attempt and drove the scope to locate the needle. The chart may show that the physician did another percutaneous access attempt with the same target, and this time gained visual confirmation. Such a chart can be displayed on a GUI of the medical system, as a digital or print report, on a mobile application, and/or similar type of output.

Another potential benefit is providing ground truth (success/fail) annotation. Phase segmentation can enable predicting if a certain percutaneous access attempt was successful or not, thereby serving as a ground truth for the case. The medical system can track a set of feature descriptors during the needle insertion phase to determine if percutaneous access has been successful. A feature descriptor can include various quantities or metrics measured by the medical system, such as needle and scope velocity, and relative pose of the needle with respect to the scope. It can also include scope articulation commands and features detected by a computer vision algorithm which detects if the needle is visible in camera view and quantifies how much anatomical motion there is. For example, there can be a direct correlation between visual confirmation and success. In one scenario, if the computer vision algorithm detects a needle in the endoscopic view, the percutaneous access attempt can be annotated or otherwise indicated as successful. In another scenario, the distance between needle and scope may be very small, but there is no visual confirmation of the needle on the scope. If the scope starts moving, it implies that the percutaneous access attempt was unsuccessful and the user is looking for the needle or driving to another calyx to select a new target. Thus, detection of the scope movement in that situation can be used to annotate or otherwise indicate that the percutaneous access attempt as unsuccessful.

Another potential benefit is providing skill assessment. Phase segmentation can enable running phase specific data analysis to assess physician skill and compute case statistics intraoperatively or postoperatively. The table below shows postoperative metrics for some of the percutaneous access phases. For example, by knowing when needle insertion starts (e.g., identified via video capture, sensor data, or the like), the medical system can determine the entry point on the skin (e.g., using kinematic data, video analysis or the like) and compute site selection metrics such as tract length (e.g., distance from skin to papilla).

| SCOPE DRIVING PHASE | | NEEDLE INSERTION PHASE | | | | | SITE SELECTION PHASE | | | | |
|---|---|---|---|---|---|---|---|---|---|---|---|
| Number of Articulation Commands | | Success Rate | | | Needle Insertion Accuracy | | Site Selection Time | | Average Tract Length | | |
| This case | All cases | Lower Pole | Mid Pole | Upper Pole | Expert Average | All cases | Expert Average | All cases | Lower Pole | Mid Pole | Upper Pole |

For example, in the scope driving phase, the user's skill can be evaluated based on the number of articulation commands received by the system. If less commands are received, that implies that the operation has gone smoothly, indicating greater skill. If more commands are received, that implies that multiple attempts have to be performed, indicating room for improvement. These metrics can also provide information on which parts of the anatomy a user struggles navigating. The number of articulations commands may be recorded and/or displayed for this operation or for multiple operations (all cases, all cases in a certain period, all cases performed by the user, etc.). For example, the medical system can generate metrics that compare by location for a given case, across physicians, and/or for the same physician over time over multiple operations.

In another example, in the needle insertion phase, the user's skill can be evaluated based on the success rate and/or the needle insertion accuracy. Success rate can be further specifically calculated based on kidney location, such as at the lower pole, mid pole, or upper pole. Needle insertion accuracy can be compared to an average value for experts. The needle insertion accuracy may be recorded and/or displayed for this operation or for multiple operations (e.g., all cases, all cases in a certain period, all cases performed by the user, etc.).

In a further example, in the site selection phase, the user's skill can be evaluated based on the site selection time or time taken by the user to select a site and average tract length. The site selection time can be compared to an average value for experts. The site selection time may be recorded and/or displayed for this operation or for multiple operations (all cases, all cases in a certain period, all cases performed by the user, etc.). Average track length can be further specifically calculated based on kidney location, such as at the lower pole, mid pole, or upper pole. Tract length for a patient may be used as an indicator of patient body mass index (BMI). This can allow case performance to be aggregated based on patient population characteristics such as BMI values or ranges.

The above table shows just some examples of possible metrics than can be evaluated. Furthermore, the above table shows just some of the specificity that can be applied to those metrics. For example, some of the specificity applied for one metric can be applied to other metrics. In some embodiments, needle insertion accuracy can be broken down further based on kidney location. Success rate can be shown with more specificity by comparing to an expert average or across multiple operations (e.g., all cases, all cases in a certain period, all cases performed by the user, etc.).

Another potential benefit of such a medical system is providing skill assessment workflow optimization. Workflow analysis can show the correlation between the sequence of workflow steps and percutaneous access success and efficiency. For example, the algorithm can compare cases where site selection was performed before target selection versus target selection performed before site selection and assess the impact to percutaneous access time and accuracy.

Such a medical system can be used in several types of procedures, including ureteroscopy. Kidney stone disease, also known as urolithiasis, is a relatively common medical condition that involves the formation, in the urinary tract, of a solid piece of material, referred to as "kidney stones," "urinary stones," "renal calculi," "renal lithiasis," or "nephrolithiasis." Urinary stones can be formed and/or found in the kidneys, the ureters, and the bladder (referred to as "bladder stones"). Such urinary stones form as a result of concentrated minerals and can cause significant abdominal pain once they reach a size sufficient to impede urine flow through the ureter or urethra. Urinary stones can be formed from calcium, magnesium, ammonia, uric acid, cysteine, and/or other compounds.

To remove urinary stones from the bladder and ureter, surgeons can insert a ureteroscope into the urinary tract through the urethra. Typically, a ureteroscope includes an endoscope at its distal end configured to enable visualization of the urinary tract. The ureteroscope can also include a lithotomy mechanism, such as the basket retrieval device, to capture or break apart urinary stones. During a ureteroscopy procedure, one physician/technician can control the position of the ureteroscope, while another other physician/technician can control the lithotomy mechanism.

In many embodiments, the techniques and systems are discussed in the context of a minimally invasive procedure. However, it should be understood that the techniques and systems can be implemented in the context of any medical procedure including, for example, percutaneous operations where access is gained to a target location by making a puncture and/or a minor incision into the body to insert a medical instrument, non-invasive procedures, therapeutic procedures, diagnostic procedures, non-percutaneous procedures, or other types of procedures. For example, such techniques can be used in tumor biopsy or ablation for urology and bronchoscopy, where an automated biopsy operation can be triggered when the system detects proximity to a suspicious site. An endoscopic procedure can include a bronchoscopy, a ureteroscopy, a gastroscopy, nephroscopy, nephrolithotomy, and so on. Further, in many embodiments, the techniques and systems are discussed as being implemented as robotically-assisted procedures. However, it should also be appreciated that the techniques and systems can be implemented in other procedures, such as in fully-robotic medical procedures.

For ease of illustration and discussion, the techniques and systems are discussed in the context of removing urinary stones, such as kidneys stones from the kidneys. However, as noted above, the techniques and systems can be used to perform other procedures.

Medical System

FIG. 1 illustrates an example medical system 100 to perform or assist in performing medical procedures in accordance with one or more embodiments. Embodiments of the medical system 100 can be used for surgical and/or diagnostic procedures. The medical system 100 includes a robotic system 110 configured to engage with and/or control a medical instrument 120 to perform a procedure on a patient

130. The medical system 100 also includes a control system 140 configured to interface with the robotic system 110, provide information regarding the procedure, and/or perform a variety of other operations. For example, the control system 140 can include a display 142 to present a user interface 144 to assist the physician 160 in using the medical instrument 120. Further, the medical system 100 can include a table 150 configured to hold the patient 130 and/or an imaging sensor 180, such as a camera, x-ray, computed tomography (CT), magnetic resonance imaging (MRI), positron emission tomography (PET) device, or the like.

In some embodiments, the physician performs a minimally-invasive medical procedure, such as ureteroscopy. The physician 160 can interact with the control system 140 to control the robotic system 110 to navigate the medical instrument 120 (e.g., a basket retrieval device and/or scope) from the urethra up to the kidney 170 where the stone 165 is located. The control system 140 can provide information via a display 142 regarding the medical instrument 120 to assist the physician 160 in navigation, such as real-time images from the medical instrument 120 or the imaging sensor 180. Once at the site of the kidney stone, the medical instrument 120 can be used to break-up and/or capture a urinary stone 165.

In some implementations of using the medical system 100, a physician 160 can perform a percutaneous procedure. To illustrate, if the patient 130 has a kidney stone 165 in a kidney 170 that is too large to be removed through a urinary tract, the physician 160 can perform a procedure to remove the kidney stone through a percutaneous access point on the patient 130. For example, the physician 160 can interact with the control system 140 to control the robotic system 110 to navigate the medical instrument 120 (e.g., a scope) from the urethra up to the kidney 170 where the stone 165 is located. The control system 140 can provide information via a display 142 regarding the medical instrument 120 to assist the physician 160 in navigating the medical instrument 120, such as real-time images from the medical instrument 120 or the imaging sensor 180. Once at the site of the kidney stone, the medical instrument 120 can be used to designate a target location for a second medical instrument (not shown) to access the kidney percutaneously (e.g., a desired point to access the kidney). To minimize damage to the kidney, the physician 160 can designate a particular papilla as the target location for entering into the kidney with the second medical instrument. However, other target locations can be designated or determined. Once the second medical instrument has reached the target location, the physician 160 can use the second medical instrument and/or another medical instrument to extract the kidney stone from the patient 130, such as through the percutaneous access point. Although the above percutaneous procedure is discussed in the context of using the medical instrument 120, in some implementations a percutaneous procedure can be performed without the assistance of the medical instrument 120. Further, the medical system 100 can be used to perform a variety of other procedures.

Minimally invasive surgery offers the potential for video recording of the operation, as a camera (e.g., a scope of a medical instrument 120) can be inserted into the body during the surgery. Additional cameras and sensors located outside the body can be used to capture video and/or data of the patient and medical system 100. For example, operating room (OR) camera(s) can capture video of activities in the operating room, such as movement of an operator's or physician's hands, location of a needle, replacement of fluidic bags, bleeding of the patient, or the like. Details such as the number of contrast injections during fluoroscopy may also be captured by the OR cameras and used to estimate the amount of radiation exposure to the patient. Audio recorded in the videos can also be used to help identify phases. For example, some robotic systems beep or otherwise make an audible noise when lasing is occurring. The videos may be archived and used later for reasons such as cognitive training, skills assessment, and workflow analysis.

Computer vision, a form of artificial intelligence (AI), allows for quantitative analysis of video by computers for identification of objects and patterns. For example, in endoscopic surgery, an AI video system can be used for gesture/task classification, skills assessment, tool type recognition, shot/event detection and retrieval. The AI system can watch a video of a surgical procedure to track the movement and timing of instruments used during the procedure. The AI system can use metrics to track the timing of tools, such as which instrument was used when, and for how long. In addition, the AI system can track the pathway of the instrument, which can be useful for evaluating procedures or identifying phases in the procedure. The AI system can determine how far the tools ranged within the surgical field, which may be correlated to the quality of surgery as better surgeons tend to handle instruments in a focused area. The AI system can also determine metrics for gauging multiple aspects of the medical professionals' performance, including their economy of motion, how often they switched back and forth between instruments, and their efficiency at each step of the procedure.

In the example of FIG. 1, the medical instrument 120 is implemented as a basket retrieval device. Thus, for ease of discussion, the medical instrument 120 is also referred to as "the basket retrieval device 120." However, the medical instrument 120 can be implemented as various types of medical instruments including, for example, a scope (sometimes referred to as an "endoscope"), a needle, a catheter, a guidewire, a lithotripter, forceps, a vacuum, a scalpel, a combination of the above, or the like. In some embodiments, a medical instrument is a steerable device, while other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments. In some embodiments, multiple medical instruments may be used. For example, an endoscope can be used with a basket retrieval device 120. In some embodiments, the medical instrument 120 may be a compound device incorporating several instruments, such as a vacuum, a basket retrieval device, a scope, or various combinations of instruments.

In some embodiments, the medical instrument 120 can include a radio-frequency identification (RFID) chip for identifying the medical instrument 120. The medical system 100 can include an RFID reader to read the RFID chip in the medical instrument to aid in identifying the instrument. Such information can be used to facilitate identifying procedures and phases. For example, if the RFID data identifies an instrument as a needle, the phase may be related to needle insertion, though determining the exact phase may require combining the RFID data with additional data, such as video, device status, telemetry (e.g., magnetic tracking, robot data, fluidics data, and/or the like).

The robotic system 110 can be configured to facilitate a medical procedure. The robotic system 110 can be arranged in a variety of ways depending on the particular procedure. The robotic system 110 can include one or more robotic arms 112 (robotic arms 112(*a*), 112(*b*), 112(*c*)) to engage with and/or control the medical instrument 120 to perform a procedure. As shown, each robotic arm 112 can include multiple arm segments coupled to joints, which can provide multiple degrees of movement. In the example of FIG. 1, the robotic system 110 is positioned proximate to the patient's 130 lower torso and the robotic arms 112 are actuated to engage with and position the medical instrument 120 for access into an access point, such as the urethra of the patient 130. With the robotic system 110 properly positioned, the medical instrument 120 can be inserted into the patient 130 robotically using the robotic arms 112, manually by the physician 160, or a combination thereof.

The robotic system 110 can also include a base 114 coupled to the one or more robotic arms 112. The base 114 can include a variety of subsystems, such as control electronics, a power source, pneumatics, an optical source, an actuator (e.g., motors to move the robotic arm), control circuitry, memory, and/or a communication interface. In some embodiments, the base 114 includes an input/output (I/O) device 116 configured to receive input, such as user input to control the robotic system 110, and provide output, such as patient status, medical instrument location, or the like. The I/O device 116 can include a controller, a mouse, a keyboard, a microphone, a touchpad, other input devices, or combinations of the above. The I/O device can include an output component, such as a speaker, a display, a haptic feedback device, other output devices, or combinations of the above. In some embodiments, the robotic system 110 is movable (e.g., the base 114 includes wheels) so that the robotic system 110 can be positioned in a location that is appropriate or desired for a procedure. In other embodiments, the robotic system 110 is a stationary system. Further, in some embodiments, the robotic system 110 is integrated into the table 150.

The robotic system 110 can be coupled to any component of the medical system 100, such as the control system 140, the table 150, the imaging sensor 180, and/or the medical instruments 120. In some embodiments, the robotic system is communicatively coupled to the control system 140. In one example, the robotic system 110 can receive a control signal from the control system 140 to perform an operation, such as to position a robotic arm 112 in a particular manner, manipulate a scope, and so on. In response, the robotic system 110 can control a component of the robotic system 110 to perform the operation. In another example, the robotic system 110 can receive an image from the scope depicting internal anatomy of the patient 130 and/or send the image to the control system 140 (which can then be displayed on the control system 140). Further, in some embodiments, the robotic system 110 is coupled to a component of the medical system 100, such as the control system 140, to receive data signals, power, and so on. Other devices, such as other medical instruments, intravenous bags, blood packs or the like can also be coupled to the robotic system 110 or other components of the medical system 100 depending on the medical procedure being performed.

The control system 140 can be configured to provide various functionality to assist in performing a medical procedure. In some embodiments, the control system 140 can be coupled to the robotic system 110 and operate in cooperation with the robotic system 110 to perform a medical procedure on the patient 130. For example, the control system 140 can communicate with the robotic system 110 via a wireless or wired connection (e.g., to control the robotic system 110, the basket retrieval device 120, receive an image(s) captured by a scope, etc.), control the flow of fluids through the robotic system 110 via one or more fluid channels, provide power to the robotic system 110 via one or more electrical connections, provide optical signals to the robotic system 110 via one or more optical fibers or other components, and so on. Further, in some embodiments, the control system 140 can communicate with a scope to receive sensor data. Moreover, in some embodiments, the control system 140 can communicate with the table 150 to position the table 150 in a particular orientation or otherwise control the table 150.

As shown in FIG. 1, the control system 140 includes various I/O devices configured to assist the physician 160 or others in performing a medical procedure. In some embodiments, the control system 140 includes an input device 146 that is employed by the physician 160 or another user to control the basket retrieval device 120. For example, the input device 146 can be used to navigate the basket retrieval device 120 within the patient 130. The physician 160 can provide input via the input device 146 and, in response, the control system 140 can send control signals to the robotic system 110 to manipulate the medical instrument 120.

In some embodiments, the input device 146 is a controller similar to a game controller. The controller can have multiple axes and buttons that can be used for controlling the robotic system 110. While the input device 146 is illustrated as a controller in the example of FIG. 1, the input device 146 can be implemented as a variety or combination of types of I/O devices, such as a touchscreen/pad, a mouse, a keyboard, a microphone, a smart speaker, etc. As also shown in FIG. 1, the control system 140 can include the display 142 to provide various information regarding a procedure. For example, the control system 140 can receive real-time images that are captured by a scope and display the real-time images via the display 142. Additionally or alternatively, the control system 140 can receive signals (e.g., analog, digital, electrical, acoustic/sonic, pneumatic, tactile, hydraulic, etc.) a medical monitor and/or a sensor associated with the patient 130, and the display 142 can present information regarding the health of the patient 130 and/or an environment of the patient 130. Such information can include information that is displayed via a medical monitor including, for example, a heart rate (e.g., electrocardiogram (ECG), heart rate variability (HRV), etc.), blood pressure/rate, muscle bio-signals (e.g., electromyography (EMG)), body temperature, oxygen saturation (e.g., $SpO_2$), carbon dioxide ($CO_2$), brainwave (e.g., electroencephalogram (EEG)), environmental temperature, and so on.

FIG. 1 also shows various anatomy of the patient 130 relevant to certain aspects of the present disclosure. In particular, the patient 130 includes kidneys 170 fluidly connected to a bladder 171 via ureters 172, and a urethra 173 fluidly connected to the bladder 171. As shown in the enlarged depiction of the kidney 170, the kidney includes calyxes 174 (e.g., major and minor calyxes), renal papillae (including the renal papilla 176, also referred to as "the papilla 176"), and renal pyramids (including the renal pyramid 178). In these examples, a kidney stone 165 is located in proximity to the papilla 176. However, the kidney stone can be located at other locations within the kidney 170.

As shown in FIG. 1, to remove the kidney stone 165 in the example minimally-invasive procedure, the physician 160 can position the robotic system 110 at the foot of the table 150 to initiate delivery of the medical instrument 120 into the patient 130. In particular, the robotic system 110 can be positioned within proximity to a lower abdominal region of the patient 130 and aligned for direct linear access to the urethra 173 of the patient 130. From the foot of the table 150, the robotic arm 112(B) can be controlled to provide access to the urethra 173. In this example, the physician 160 inserts a medical instrument 120 at least partially into the urethra along this direct linear access path (sometimes referred to as "a virtual rail"). The medical instrument 120 can include a lumen configured to receive the scope and/or basket retrieval device, thereby assisting in insertion of those devices into the anatomy of the patient 130.

Once the robotic system 110 is properly positioned and/or the medical instrument 120 is inserted at least partially into the urethra 173, the scope can be inserted into the patient 130 robotically, manually, or a combination thereof. For example, the physician 160 can connect the medical instrument 120 to the robotic arm 112(C). The physician 160 can then interact with the control system 140, such as the input device 146, to navigate the medical instrument 120 within the patient 130. For example, the physician 160 can provide input via the input device 146 to control the robotic arm 112(C) to navigate the basket retrieval device 120 through the urethra 173, the bladder 171, the ureter 172, and up to the kidney 170.

The control system 140 can include various components (sometimes referred to as "subsystems") to facilitate its functionality. For example, the control system 140 can include a variety of subsystems, such as control electronics, a power source, pneumatics, an optical source, an actuator, control circuitry, memory, and/or a communication interface. In some embodiments, the control system 140 includes a computer-based control system that stores executable instructions, that when executed, implement various operations. In some embodiments, the control system 140 is movable, such as that shown in FIG. 1, while in other embodiments, the control system 140 is a stationary system. Although various functionality and components are discussed as being implemented by the control system 140, any of this functionality and/or components can be integrated into and/or performed by other systems and/or devices, such as the robotic system 110 and/or the table 150.

The medical system 100 can provide a variety of benefits, such as providing guidance to assist a physician in performing a procedure (e.g., instrument tracking, patient status, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. Further, the medical system 100 can provide non-radiation-based navigational and/or localization techniques to reduce physician exposure to radiation and/or reduce the amount of equipment in an operating room. Moreover, the medical system 100 can divide functionality into the control system 140 and the robotic system 110, each of which can be independently movable. Such a division of functionality and/or movability can enable the control system 140 and/or the robotic system 110 to be placed at locations that are optimal for a particular medical procedure, which can maximize working area around the patient, and/or provide an optimized location for a physician to perform a procedure. For example, many aspects of the procedure can be performed by the robotic system 110 (which is positioned relatively close to the patient) while the physician manages the procedure from the comfort of the control system 140 (which can be positioned farther way).

In some embodiments, the control system 140 can function even if located in a different geographic location from the robotic system 110. For example, in a tele-health implementation, the control system 140 is configured to communicate over a wide area network with the robotic system 110. In one scenario, a physician 160 may be located in one hospital with the control system 140 while the robotic system 110 is located in a different hospital. The physician may then perform the medical procedure remotely. This can be beneficial where remote hospitals, such as those in rural areas, have limited expertise in particular procedures. Those hospitals can then rely on more experienced physicians in other locations. In some embodiments, a control system 140 is able to pair with a variety of robotic systems 110, for example, by selecting a specific robotic system and forming a secure network connection (e.g., using passwords, encryption, authentication tokens, etc.). Thus, a physician in one location may be able to perform medical procedures in a variety of different locations by setting up a connection with robotic systems 110 located at each of those different locations.

In some embodiments, the robotic system 110, the table 150, the medical instrument 120, the needle and/or the imaging sensor 180 are communicatively coupled to each other over a network, which can include a wireless and/or wired network. Example networks include one or more personal area networks (PANs), one or more local area networks (LANs), one or more wide area networks (WANs), one or more Internet area networks (IANs), one or more cellular networks, the Internet, etc. Further, in some embodiments, the control system 140, the robotic system 110, the table 150, the medical instrument 120, and/or the imaging sensor 180 are connected for communication, fluid/gas exchange, power exchange, and so on via one or more support cables.

Although not illustrated in FIG. 1, in some embodiments the medical system 100 includes and/or is associated with a medical monitor configured to monitor the health of the patient 130 and/or an environment in which the patient 130 is located. For example, a medical monitor can be located in the same environment where the medical system 100 is located, such as within an operating room. The medical monitor can be physically and/or electrically coupled to one or more sensors that are configured to detect or determine one or more physical, physiological, chemical, and/or biological signals, parameters, properties, states and/or conditions associated with the patient 130 and/or the environment. For example, the one or more sensors can be configured to determine/detect any type of physical properties, including temperature, pressure, vibration, haptic/tactile features, sound, optical levels or characteristics, load or weight, flow rate (e.g., of target gases and/or liquid), amplitude, phase, and/or orientation of magnetic and electronic fields, constituent concentrations relating to substances in gaseous, liquid, or solid form, and/or the like. The one or more sensors can provide the sensor data to the medical monitor and the medical monitor can present information regarding the health of the patient 130 and/or the environment of the patient 130. Such information can include information that is displayed via a medical monitor including, for example, a heart rate (e.g., ECG, HRV, etc.), blood pressure/rate, muscle bio-signals (e.g., EMG), body temperature, oxygen saturation (e.g., $SpO_2$), $CO_2$, brainwave (e.g., EEG), environmental temperature, and so on. In some embodiments, the medical monitor and/or the one or more sensors are coupled to the control system 140 and the control system 140 is configured to provide information regarding the health of the patient 130 and/or the environment of the patient 130.

Urinary Stone Capture

Figure 2A:
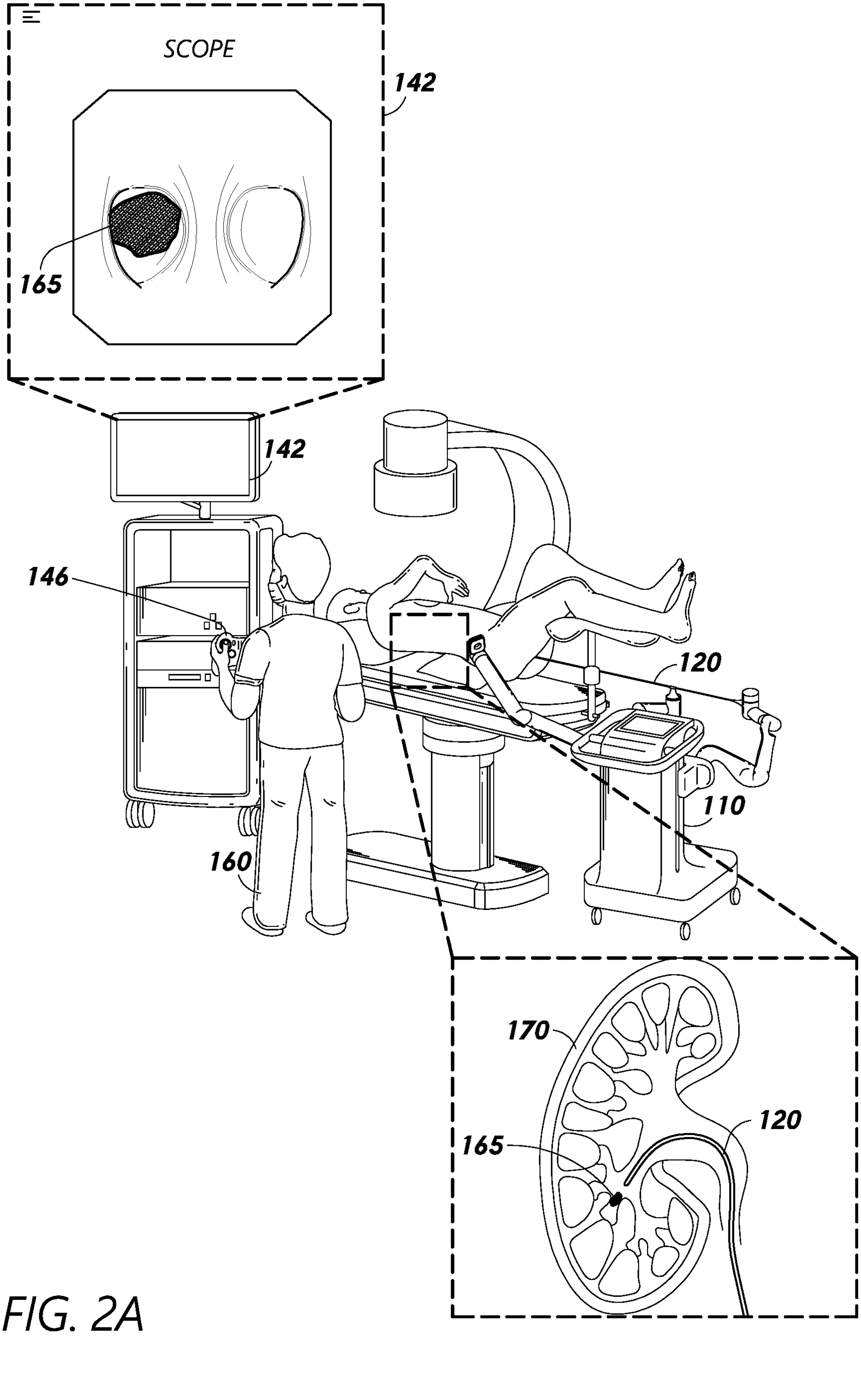
FIGS. 2A-2B illustrate a perspective view of the medical system while performing a urinary stone capture procedure, according to certain embodiments.
Figure 2B:
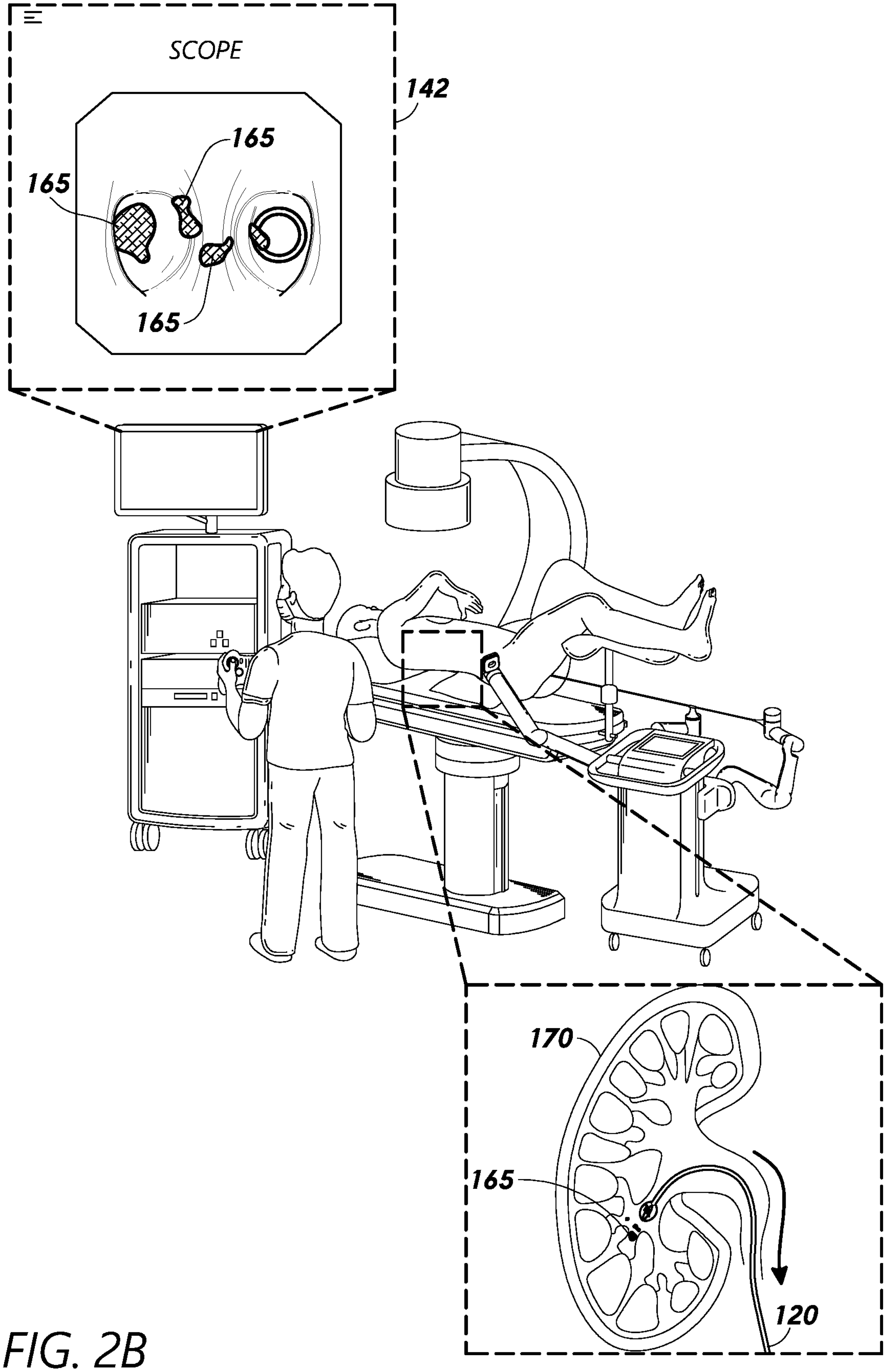

FIGS. 2A-2B illustrate a perspective view of the medical system 100 while performing a urinary stone capture procedure. In these examples, the medical system 100 is arranged in an operating room to remove a kidney stone from the patient 130. In many instances of such a procedure, the patient 130 is positioned in a modified supine position with the patient 130 slightly tilted to the side to access the posterior or side of the patient 130. The urinary stone capture procedure may also be performed with the patient in a regular supine position, as show in in FIG. 1. Although FIGS. 2A-2B illustrate the use of the medical system 100 to perform a minimally-invasive procedure to remove a kidney stone from the patient 130, the medical system 100 can be used to remove a kidney stone in other manners and/or to perform other procedures. Further, the patient 130 can be arranged in other positions as desired for a procedure. Various acts are described in FIGS. 2A-2B and throughout this disclosure as being performed by the physician 160. It should be understood that these acts can be performed directly by the physician 160, indirectly by the physician with the aid of the medical system 100, by a user under the direction of the physician, by another user (e.g., a technician), and/or any other user.

Although particular robotic arms of the robotic system 110 are illustrated as performing particular functions in the context of FIGS. 2A-2B, any of the robotic arms 112 can be used to perform the functions. Further, any additional robotic arms and/or systems can be used to perform the procedure. Moreover, the robotic system 110 can be used to perform other parts of the procedure.

As shown in FIG. 2A, the basket retrieval device 120 is maneuvered into the kidney 170 to approach the urinary stone 165. In some scenarios, the physician 160 or other user uses the input device 146 to directly control movement of the basket retrieval device 120. Such directly controlled movement can include insertion/retraction, flexing the basket retrieval device 120 left or right, rotation, and/or regular open/close of the basket. Using various movements, the basket retrieval device 120 is placed close to the stone.

In some embodiments, a laser, shock wave device, or other device is used to break up the stone. The laser or other device may be incorporated into the basket retrieval device 120 or may be a separate medical instrument. In some situations, the stone 165 is small enough that breaking up the stone into smaller pieces is not needed.

As shown in FIG. 2B, the open basket is maneuvered to surround the urinary stone 165 or a smaller piece of the urinary stone. The basket retrieval device 120 is then withdrawn from the kidney 170 and then out of the patient's body.

If additional stones (or large pieces of a broken-up stone 165) exist, the basket retrieval device 120 may be reinserted into the patient to capture the remaining large pieces. In some embodiments, a vacuum instrument can be used to facilitate removal of the pieces. In some situations, the stone pieces may be sufficiently small that they can be passed by the patient naturally.

Phase Segmentation and Phase Recognition

Automated surgical workflow analysis can be used to detect different phases in a procedure and to assess surgical skill and procedural efficiency. Data collected during procedures (e.g. video data) can be segmented into multiple sections using, for example, machine learning methods, including but not limited to, a hidden Markov model (HMM) and a long-term-short-memory (LTSM) network.

In surgical phase segmentation, captured medical procedure data is automatically segmented into phases, using input data from the operating room to identify the phases. Segmentation may be done in real-time during the procedure or performed post-operatively on recorded data. In one embodiment, the surgical data can be preprocessed using dynamic time warping to divide the phases into equal comparable segments. The input data can consist of instrument signals, annotations, tracking of instruments (e.g. EM), or information obtained from videos.

Figure 3:
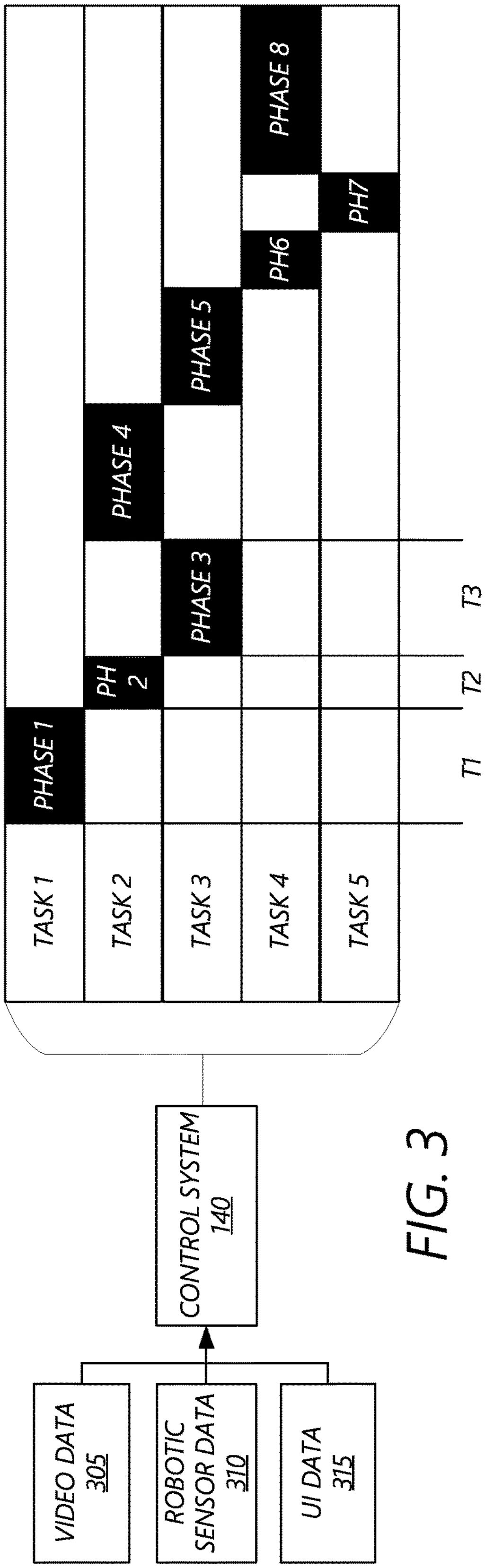
FIG. 3 illustrates a block diagram of a control system of the medical system, with associated inputs and outputs, according to certain embodiments.
Figure 4A:
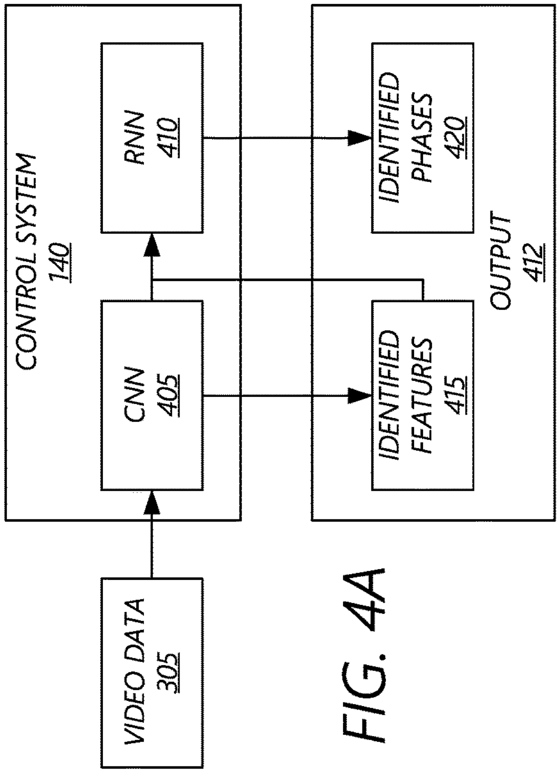
FIG. 4A illustrates a block diagram of a control system configured to utilize machine learning to generate outputs from video data, according to certain embodiments.
Figure 4B:
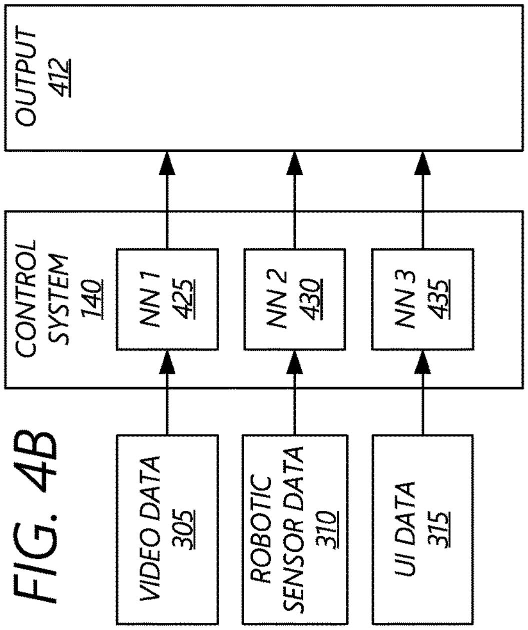
FIG. 4B illustrates a block diagram of a control system configured to utilize machine learning to generate outputs from several types of data, according to certain embodiments.

Recognition of surgical workflow can be done at different granularity levels, depending on the procedure. It can be done on phases and steps (higher level), or gestures and activities (lower level). Surgical phase recognition can be performed on time series, kinematic data, and video data using machine learning approaches such as HMMs, Gaussian Mixture Models (GMMs), and Support Vector Machines (SVMs), as well as deep learning-based approaches for phase recognition from video data using Convolutional Neural Networks (CNNs). For surgical gesture and activity recognition, similar methods (SVMs, Markov models) can be used on mainly video data or a combination of video and kinematic data, as well as more recent deep-learning based methods such as CNNs that can be used for recognition of tool presence, tasks, and activities in video data. Phase segmentation can use multiple data sources to segment the case data to different subtasks as shown in FIG. 3 or use a single data source, such as video, to classify the current phase as shown in FIG. 4A. In FIG. 4B, additional data (e.g., sensor data or UI data) can then be incorporated to further refine the output produced by the control system 140.

In FIG. 3, the control system 140 receives various input data from the medical system 100. Such input can include video data 305 captured by the imaging sensor 180, robotic sensor data 310 from one or more sensors of the robotic system 110, and user interface (UI) data received from the input device 146.

Video data 305 can include video captured from scopes deployed within a patient, video captured from cameras in the operating room, and/or video captured by cameras of the robotic system 110. Robotic sensor data 310 can include kinematic data from the robotic system 110 (e.g., using vibration, accelerometer, positioning, and/or gyroscopic sensors), device status, temperature, pressure, vibration, haptic/tactile features, sound, optical levels or characteristics, load or weight, flow rate (e.g., of target gases and/or liquid), amplitude, phase, and/or orientation of magnetic and electronic fields, constituent concentrations relating to substances in gaseous, liquid, or solid form, and/or the like. UI data 315 can include button presses, menu selections, page selections, gestures, voice commands, and/or the like made by the user and captured by input devices of the medical system 100. Patient sensor data, such as those described in FIG. 1 above, may also be used as an input to the control system 140.

The control system 140 can analyze the video data 305 (e.g., using machine learning algorithms), as well as using robotic sensor data 310 and UI data 315 to identify phases of the a medical procedure. In one example, a medical procedure such as ureteroscopy includes several tasks (e.g., Task 1-Task 5). Each task may be performed in one or more phases of the medical procedure. In the example shown in FIG. 3, Task 1 is performed in phase 1. Task 2 is performed in phase 2 and 4. Task 3 is performed in phase 3 and phase 5. Task 4 is performed din phase 6 and 8. Task 5 is performed in phase 7. Time 1 (T1) denotes the time taken to complete phase 1, Time 2 (T2) denotes the time taken to complete phase 2, and time 3 (T3) denotes the time taken to complete phase 3. Other procedures may have a different number of tasks and/or a different number of phases.

For robotic procedures where there are manual and automated task, surgical phase detection can be used to make the transition between manual and automated tasks automatic and seamless. For example, T1 may correspond to a manual task, T2 may be an automated task, and T3 may again be a manual task. In one embodiment, when the target selection phase is active, the target selection step can be autonomously performed by the robot driving the scope. Alternatively, the user can perform site selection by picking a point on the skin using an EM marker, and the robot can autonomously align the needle to the target insertion trajectory.

FIG. 4A illustrates a block diagram of the control system 140 configured to utilize machine learning to generate outputs from video data from a medical procedure, according to certain embodiments. In some embodiments, the control system 140 is configured to process the video data 305 first, using machine learning algorithms. In one embodiment, video data 305 is processed by a CNN 405 to generate output 412 to identify features recorded in the video, such as surgical tools, stone(s), human anatomy (e.g., papilla), or the like. Such identified features 415 may be provided as input to a recurrent neural networks (RNN) 410, along with the original video. The RNN 410 can then process the video data 305 and the identified features 415 to generate output 412 to identify phases 420 in a medical procedure.

Supplemental data such as robotic sensor data 310 or UI data 315 may then be used to further refine (e.g., increase accuracy or increase the number of identifications) the identified features 415 and the identified phases 420. In other embodiments, the robotic sensor data 310 and/or UI data 315 can be used prior to the processing of the video data 305 by the control system 140 to narrow the possible options considered by the control system 140. For example, the supplemental data can be used to identify a specific procedure, which narrows the universe of possible tasks and phases to those corresponding to the specific procedure. The control system 140 may then limit the identified features 415 and identified phases 420 to those that correspond to the specific procedure. For example, if a task is initially identified in the video data 305 by the control system 140, but that task is not associated with the specific procedure, the control system 140 may reprocess the video until the task is re-identified as a task corresponding to the specific procedure.

After completing processing of the video data 305, the control system 140 may generate an annotated video that includes the identified features 415 and/or identified phases 420. Such annotations may be stored as part of the video (e.g., in the same video file), meta-data stored alongside the video, in a database, and/or other data format.

By creating meta-data enhanced video, the video becomes easier to use for reviewing medical procedures. For example, a viewer can jump forward or backward to specific phase of interest rather than manually searching for when a specific phase occurred. In addition, multiple videos can be more easily processed to aggregate data and generate metrics. For example, multiple videos can be searched for instances of a particular phase (e.g., needle insertion or stone capture), and analyzed to generate metrics about the that phase (e.g., success rates, average attempts, number of attempts, etc.).

While FIG. 4A shows video data 305 being processed by the control system 140, other types of data can be processed by the control system 140, serially or in tandem with each other. For example, such data can include instrument positioning as measure by electromagnetic tracking sensors, robotic system 110 data such as how far the scope is inserted, how the scope is articulated, if basket is open or closed, how far the basket is inserted, and/or the connection status of the robotic system. The data can be provided as input to a single neural network or to multiple neural networks. For example, each different type of sensor (e.g., video, device status, telemetry such as: magnetic tracking; robot data; and/or fluidics data) may have its own network and the outputs of the networks may be concatenated before the final phase classification layer to obtain a single phase prediction.

FIG. 4B illustrates one such embodiment where different types of data from different devices and/or sensors are processed by different neural networks. Video data 305 can be processed by a first neural network 425 (e.g., CNN and/or RNN as described in FIG. 4A), robotic sensor data 310 can be processed by a second neural network 430, and UI data can be processed by a third neural network 435. The outputs from the different neural networks may then be combined to generate an output 412 (e.g., phase prediction) for the medical system 100.

Phase Identification Process

Figure 5:
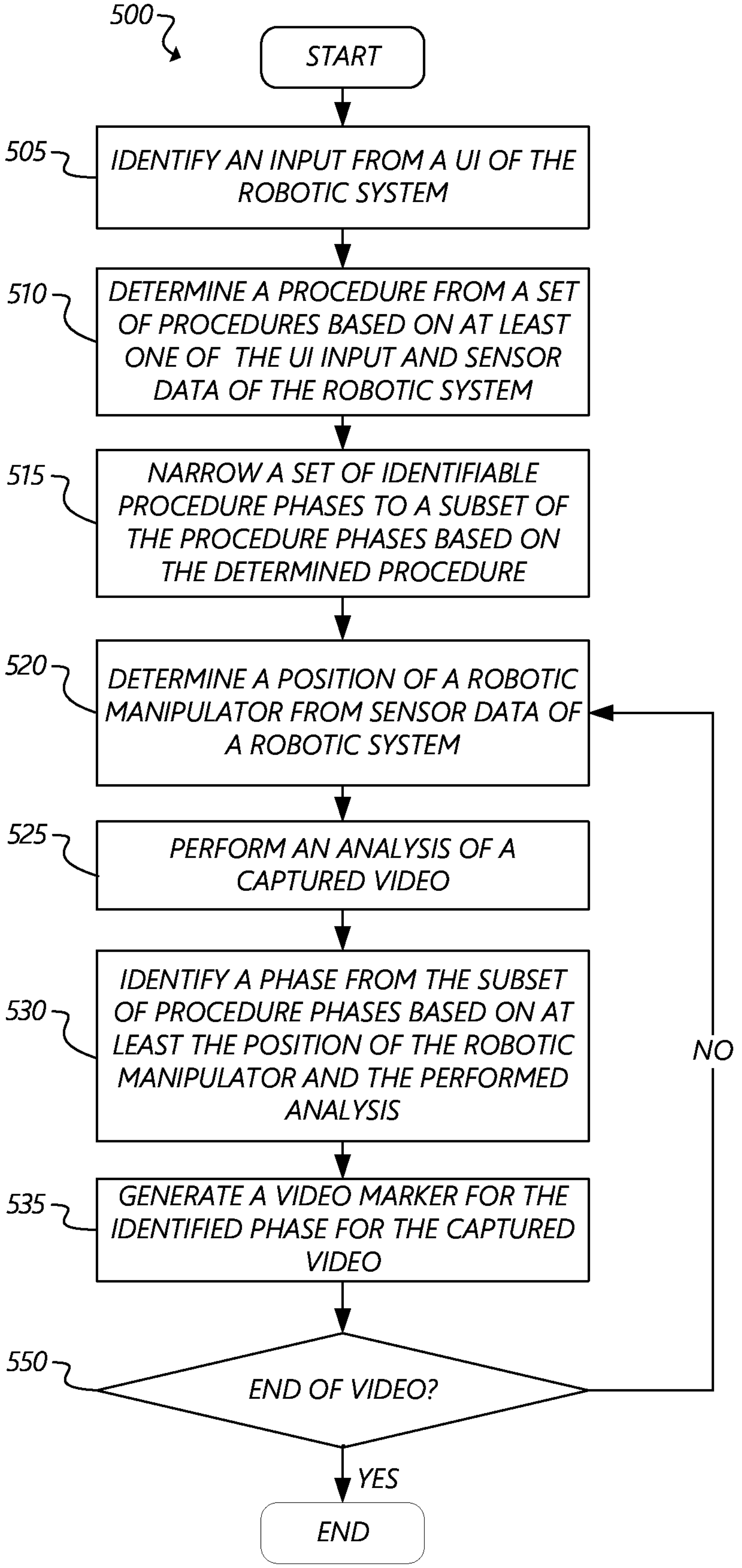
FIG. 5 is a flow diagram of a phase identification process, according to certain embodiments.

FIG. 5 is a flow diagram of a phase identification process 500, according to certain embodiments. The phase identification process 500 can be performed by the control system 140 or by another component of the medical system 100 of FIG. 1. While the following describes one possible sequence to the process, other embodiments can perform the process in a different order or may include additional steps or may exclude one or more of the steps described below.

At block 505, the control system 140 identifies an input from a UI of the robotic system. For example, the input may be received from an input device 146 such as controller or touch screen. Possible inputs can include selection of a procedure phase or of a UI screen associated with a specific procedure phase. For example, a first screen may list options for a first procedure, while a second screen may list options for second procedure. If the user is making selections on the first screen, then those selections indicate the user will be performing the first procedure. If the user is making selections on the second screen, then those selections indicate the user will be performing the second procedure. Thus, by organizing the screens of the UI to correspond to particular phases, the control system 140 can obtain phase information based on the user's selections. In another example, one embodiment of the medical system 100 can include a UI with a first screen showing selectable stone management procedures, such as ureteroscopy, percutaneous access or mini percutaneous nephrolithotomy (PCNL). If the user selects ureteroscopy, the control system 140 can determine that the phases are related to ureteroscopy (e.g., basketing, lasing and/or surveying the kidney). Likewise, selecting the other stone management procedures indicates the phases are related to the corresponding procedures.

At block 510, the control system 140 determines a procedure from a set of procedures based on at least one of the UI input and sensor data. As described above, the input from the UI interface can be used to identify the current possible procedure phase. In addition, robotic sensor data can also be used to identify the procedure. For example, if an arm of the robotic system 110 is determined to be approaching the patient while holding a surgical instrument, the control system 140 may determine that the current procedure is related to insertion of a medical instrument.

At block 515, the control system 140 can narrow the set of identifiable procedure phases to a subset of the procedure phases based on the determined procedure. For example, lasing may be associated with tasks or phases such as activating a laser or stopping the laser. Basketing may be associated with tasks or phases such as capturing a stone or retracting the basket. Insertion of a medical instrument 120 may be associated with aligning the instrument with the target and inserting the instrument into the target site. In one example, if the control system 140 determines the current procedure is basketing during ureteroscopy, the control system 140 can narrow the possible phases to capturing a stone or retracting the basket.

At block 520, the control system 140 can determine a position of a robotic manipulator (e.g., robotic arm 112) from sensor data of the robotic system 110. As described in FIG. 3, various types of sensors can be used to generate sensor data, which may then be used to determine the position.

At block 525, the control system 140 can perform an analysis of a captured video. In some embodiments, such as those described in FIG. 4A, machine learning algorithms are used to perform the analysis and generate output such as identified features and provisional identification of phases. Outputs can include identification of physical objects such as surgical tools or parts of the anatomy. For example, if the control system 140 identifies a ureter in the captured video, that indicates the phase is not related to percutaneous access. Similarly, identifying papilla indicates the phase is not related to basketing. Identification of other types of anatomy can similarly be used to eliminate the possibility of certain phases.

At block 530, the control system 140 can identify a phase from the subset of procedure phases based on at least the position of the robotic manipulator and the performed analysis. For example, if the control system 140 is receiving basketing inputs via a controller, the control system 140 can determine that the phase is one of the basketing phases. In addition, if the performed analysis identifies that the captured video is showing a basket approaching a broken-up kidney stone, the control system 140 can determine that the current phase is capturing the stone. In another example, if the performed analysis identifies that the captured video is showing a basket withdrawing from the broken-up kidney stone, the control system 140 can determine that the current phase is retracting the basket into a sheath. In a further example, kinematic data from the robotic system 110 may indicate a medical instrument is being withdrawn from within the patient and the control system 140 may determine that the current phase is retracting the basket into a sheath.

At block 535, the control system 140 can generate a video marker for the identified phase for the captured video. The video marker may be embedded as meta-data in the same file as the video, as a separate file associated with the video file, as meta-data stored in a database for video annotations, or the like.

In some embodiments, the video file is annotated such that viewers of the video file can jump to specific phases in the video. For example, the video may be divided into chapters or segments corresponding to the different phases. In one embodiment, a seek bar for the video may be marked with colored segments corresponding to different phases, where each phase is denoted by a different color.

At block 550, the control system 140 can determine if the end of the video is reached. If yes, the process 500 can end. If no, the process 500 can loop back to block 520 to continue identifying additional phases. For example, the process 500 may loops once, twice, three times, or more to identify a first phase, a second phase, a third phase, or more phases. Subsequently, the captured video may end up with one or more video markers, depending on the number of phases identified.

Triggering Automated Actions

Figure 6:
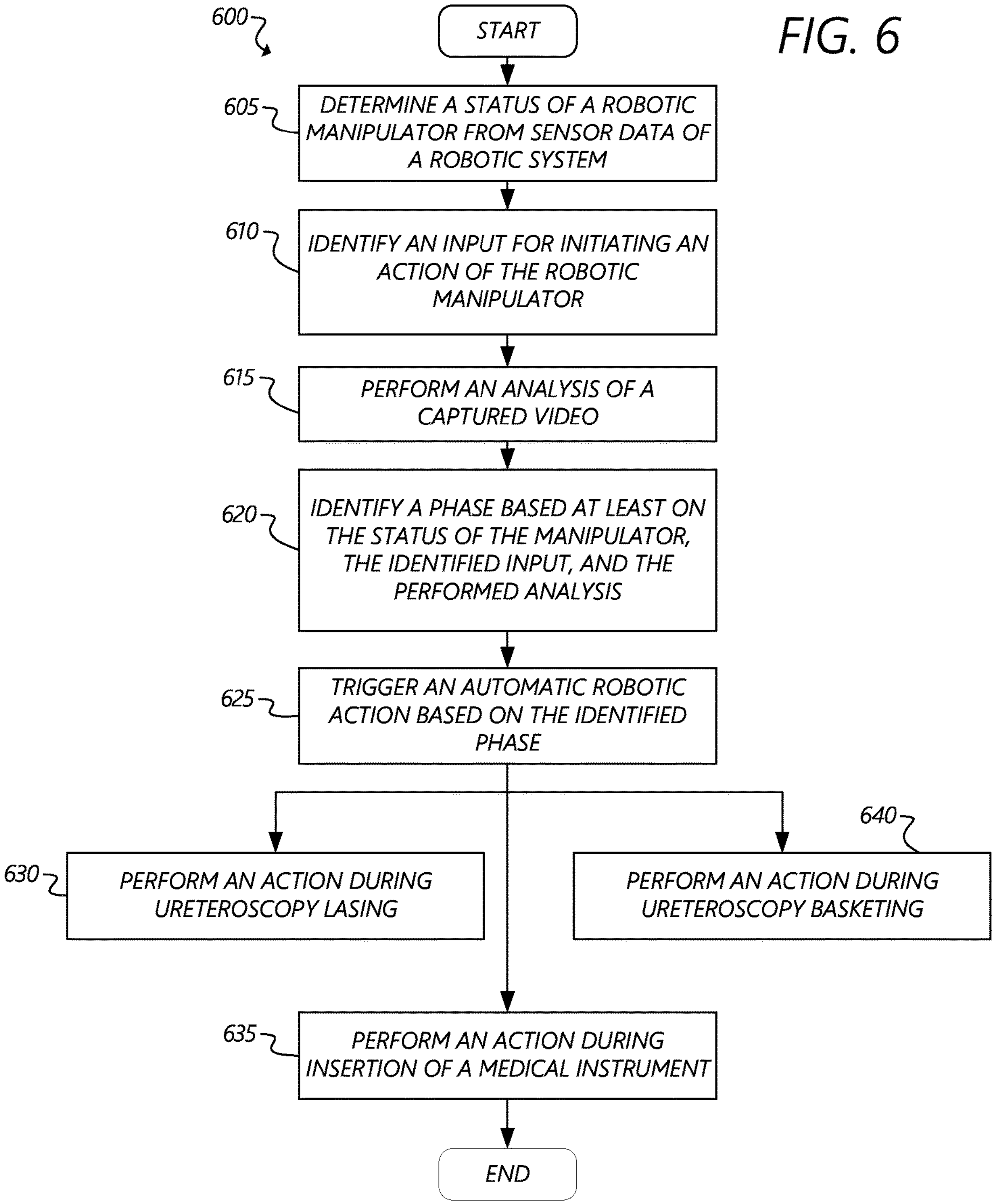
FIG. 6 is a flow diagram of a triggering process for automated robotic action, according to certain embodiments.

FIG. 6 is a flow diagram of a triggering process 600 for automated robotic action, according to certain embodiments. The triggering process 600 can be performed by the control system 140 or by another component of the medical system 100 of FIG. 1. While the following describes one possible sequence to the process, other embodiments can perform the process in a different order or may include additional steps or may exclude one or more of the steps described below.

At block 605, the control system 140 can determine a status of a robotic manipulator (e.g., robotic arm 112) from sensor data (e.g., kinematic data) of the robotic system 110. As described in FIG. 3, various types of sensors can be used to generate sensor data, which may then be used to determine the position or other status of the robotic manipulator.

At block 610, the control system 140 can determine an input for initiating an action of the robotic manipulator. For example, the input may be from a user manipulating a controller to control a basketing device. In another example, the input may be a screen selection or a menu selection on a UI of the medical system 100.

At block 615, the control system 140 can perform an analysis of a captured video. In some embodiments, such as those described in FIG. 4A, machine learning algorithms are used to perform the analysis and generate output such as identified features and provisional identification of phases.

At block 620, the control system 140 can identify a phase of medical procedure based at least on the status of the manipulator, the identified input, and the performed analysis. For example, if the control system 140 is receiving basketing inputs via a controller, the control system 140 can determine that the phase is one of the basketing phases. In addition, if the performed analysis identifies that the captured video is showing a basket approaching a broken-up kidney stone, the control system 140 can determine that the current phase is capturing the stone. In another example, if the performed analysis identifies that the captured video is showing a basket withdrawing from the broken-up kidney stone, the control system 140 can determine that the current phase is retracting the basket into a sheath. In a further example, kinematic data from the robotic system 110 may indicate a medical instrument is being withdrawn from within the patient and the control system 140 may determine that the current phase is retracting the basket into a sheath.

Figure 7:
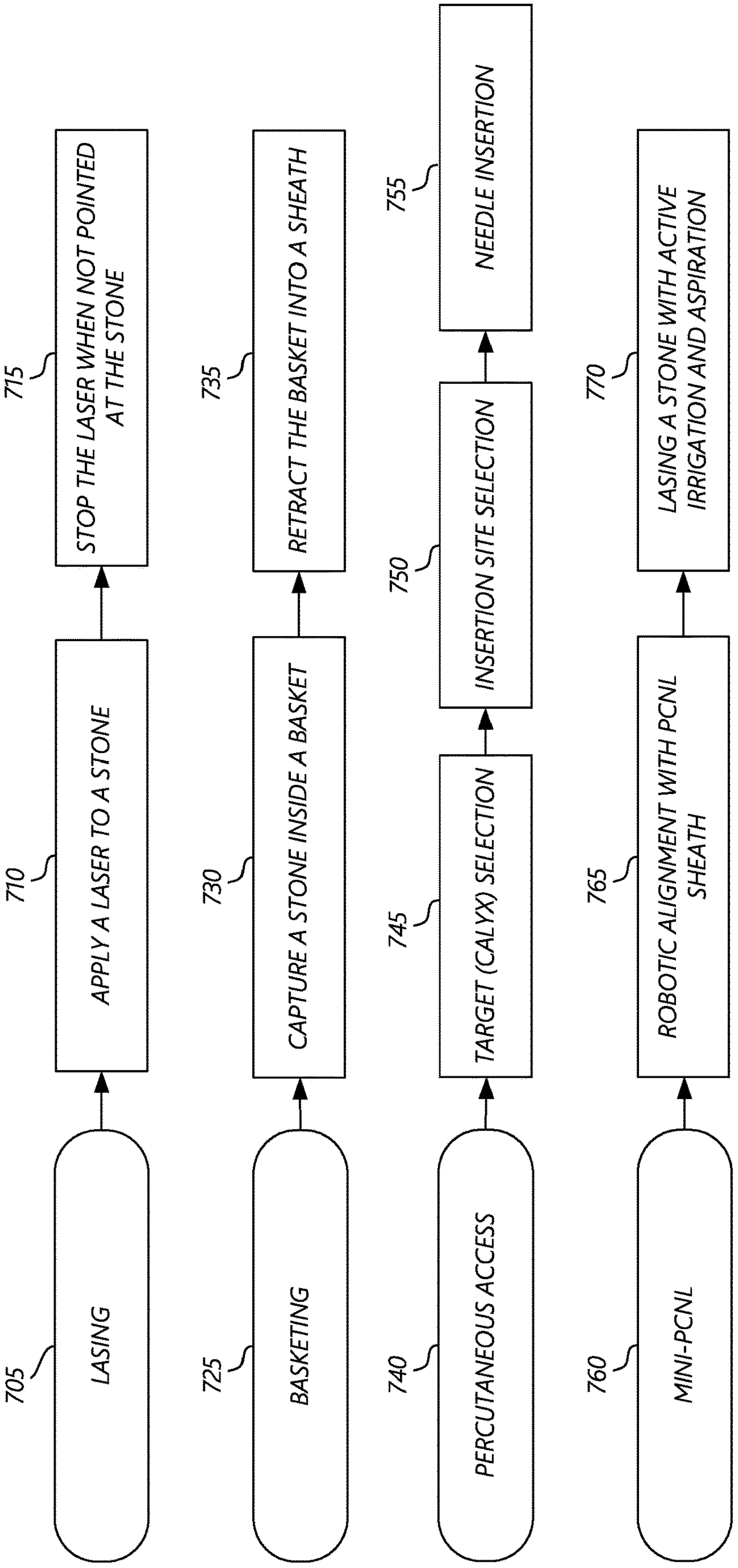
FIG. 7 is a diagram showing different types of triggered actions of the robotic system, according to certain embodiments.

At block 625, the control system 140 can trigger an automatic action of the robotic system 110 based on the identified phase. The triggered action can vary based on the type of procedure being performed. Some possible actions are shown in blocks 630, 635, and 640. At block 630, the robotic system 110 performs an action during ureteroscopy lasing. At block 635, the robotic system 110 performs an action during insertion of a medical instrument, such as a needle. At block 635, the robotic system 110 performs an action during ureteroscopy basketing. After causing an action by the robotic system 110, the triggering process 600 can end. FIG. 7 describes additional detail on specific actions that may be triggered.

FIG. 7 is a diagram showing different types of triggered actions of the robotic system 110, according to certain embodiments. The actions may be triggered in response to identifying a current phase of an operation or identifying a user action. In some embodiments, the actions may be fully automatic and performed without needing additional input from a user. In other embodiments, the actions may be partially automated, requiring confirmation from the user before being performed by the robotic system 110. Different combinations of the phases may be performed based on the procedure being performed by the robotic system 110. Some example procedures include (retrograde) ureteroscopy, percutaneous nephrostolithotomy (PCNL), mini-PCNL or the like. For example, ureteroscopy can include a surveying phase (not shown), a lasing phase, and a basking phase. PCNL can include a percutaneous access phase, a surveying phase, a lasing phase and a basketing phase. Mini-PCNL can include additional alignment and/or aspiration phases.

For example, during lasing 705, actions that can be triggered include applying a laser to a stone 710 and stopping the laser when not pointed at the stone 715. In one scenario, the robotic system 110, using various sensors (e.g., a camera), can detect when the laser is pointed at the stone. It may then determine the size of the stone, for example, by using machine learning algorithms that have been trained using recordings of previous ureteroscopy procedures or by using traditional computer vision algorithms (e.g., comparing the known size of the basket with the size of the stone). Based on the determined size, the robotic system 110 can then determine an initial lasing time based on recorded lasing times for similar sized and/or types of stones. The robotic system 110 can then stop the laser after the determined lasing time or if it detects that the stone has broken up. In other scenarios, the user may provide additional input, such as setting the lasing time or providing permission for the laser to be activated by the robotic system.

In another scenario, applying the laser may be triggered by the user while the stopping the laser is triggered automatically by the robotic system 110. For example, the robotic system 110, using its sensors, can detect when the targeting of the laser drifts from the stone or is otherwise not centered on the stone and stop the laser in response.

In another example, during basketing 725, actions that can be triggered include capturing a stone inside a basket 730 and retracing the basket into a sheath 735. In one scenario, the robotic system 110 can trigger actuation of the basket 730 when it detects that the basket 730 is aligned with the stone and within a specified distance. The basket 730 can then be actuated to capture the stone. The robotic system 110, using its sensors (e.g., camera or pressure sensors) can then determine if the stone is captured inside the basket 730 and trigger the retraction of the basket into the sheath 735. The user may then retract the sheath from the patient's body, thereby removing the stone. In another example, during percutaneous access 740, actions that can be triggered include target (calyx) selection 745, insertion site selection 750, and needle insertion 755 into the target site. In one scenario, the robotic system 110 can determine the target and the insertion site at the target (e.g., marked by the user or identified by the system). The robotic system 110 may then wait for confirmation from the user to proceed. After receiving confirmation, the robotic system 110 may then insert the needle (or other instrument) into the target site.

In another example, during a mini_PCNL procedure, additional phases can include robotic alignment with a PCNL sheath 765 and lasing a stone with active irrigation and aspiration 770. Triggered actions in these phases can include aligning an instrument with the PCNL sheath and increasing aspiration. For example, if the robotic system 110 detects an increase in stone fragments during lasing or otherwise greater dusting that limits visibility, the robotic system 110 can increase aspiration or suction to remove more of the stone fragments. Once visibility or field of view increases, the robotic system 110 can reduce aspiration.

While the above has discussed some examples and scenarios of automatic actions of the robotic system 110 that can be triggered based on the identified phase, the triggerable actions are not limited to the actions discussed above. The robotic system 110 may be programmed to perform other triggerable actions based on the needs of the users and patients.

Evaluating Tasks Performed During Phases

Figure 8:
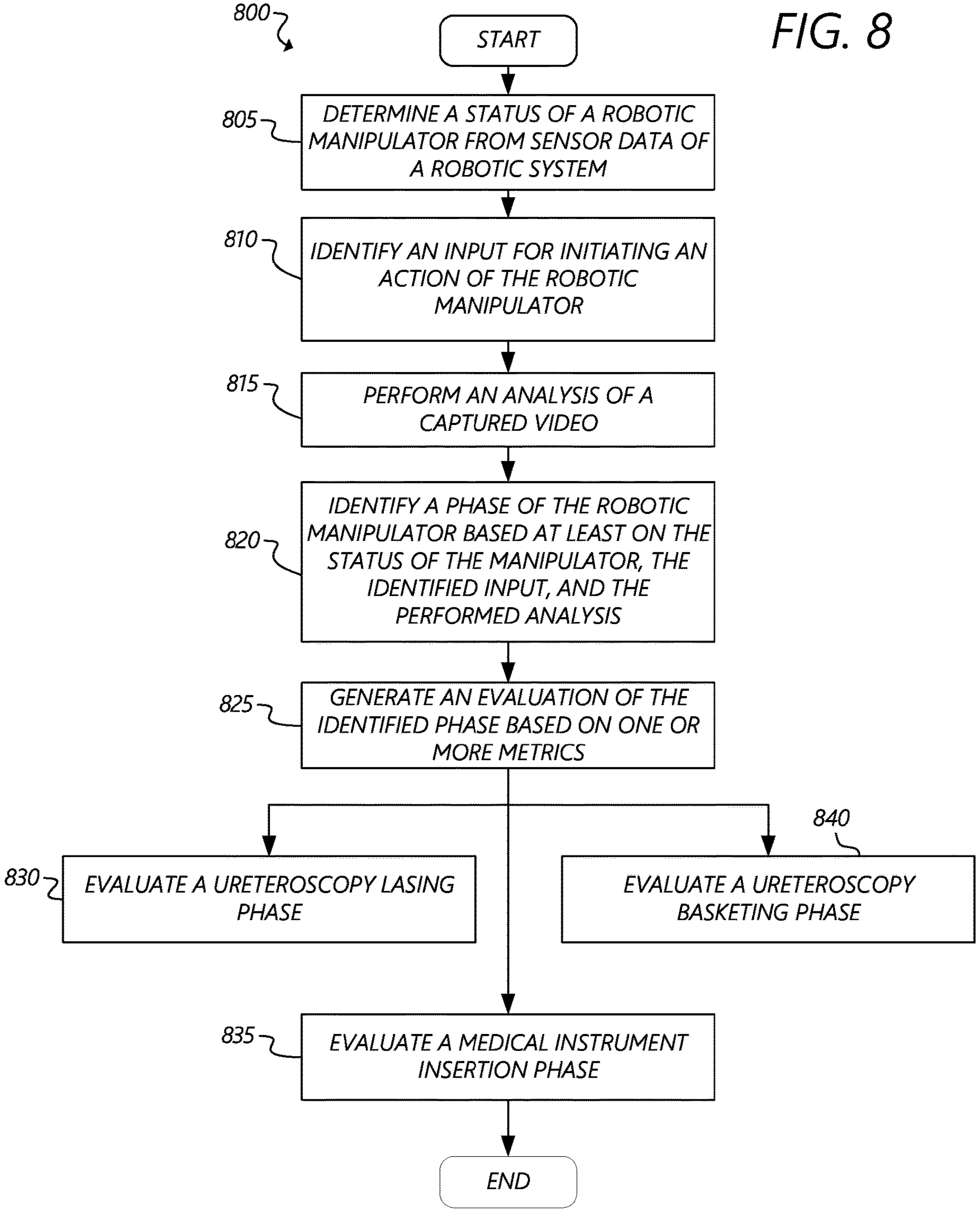
FIG. 8 is a flow diagram of an evaluation process for tasks performed during identified phases, according to certain embodiments.

FIG. 8 is a flow diagram of an evaluation process 800 for tasks performed during identified phases, according to certain embodiments. The evaluation process 800 can be performed by the control system 140 or by another component of the medical system 100 of FIG. 1. While the following describes one possible sequence to the process, other embodiments can perform the process in a different order or may include additional steps or may exclude one or more of the steps described below.

At block 805, the control system 140 can determine a status of a robotic manipulator (e.g., robotic arm 112) from sensor data of the robotic system 110. As described in FIG. 3, various types of sensors can be used to generate sensor data, which may then be used to determine the position or other status of the robotic manipulator.

At block 810, the control system 140 can determine an input for initiating an action of the robotic manipulator. For example, the input may be from a user manipulating a controller to control a basketing device. In another example, the input may be a screen selection or a menu selection on a UI of the medical system 100.

At block 815, the control system 140 can perform an analysis of a captured video. In some embodiments, such as those described in FIG. 4A, machine learning algorithms are used to perform the analysis and generate output such as identified features and provisional identification of phases.

At block 820, the control system 140 can identify a phase of medical procedure based at least on the status of the manipulator, the identified input, and the performed analysis. For example, if the control system 140 is receiving basketing inputs via a controller, the control system 140 can determine that the phase is one of the basketing phases. In addition, if the performed analysis identifies that the captured video is showing a basket approaching a broken-up kidney stone, the control system 140 can determine that the current phase is capturing the stone. In another example, if the performed analysis identifies that the captured video is showing a basket withdrawing from the broken-up kidney stone, the control system 140 can determine that the current phase is retracting the basket into a sheath. In a further example, kinematic data from the robotic system 110 may indicate a medical instrument is being withdrawn from within the patient and the control system 140 may determine that the current phase is retracting the basket into a sheath.

At block 825, the control system 140 can generate an evaluation of the identified phase based on one or more metrics. The evaluated phase can vary based on the type of procedure being performed. Some possible phases are shown in blocks 830, 835, and 840. At block 830, the control system 140 evaluates a ureteroscopy lasing phase. At block 835, the control system 140 evaluates a medical instrument insertion phase. At block 840, the control system 140 evaluates a ureteroscopy basketing phase. Some specific examples of various evaluations are described below.

Figure 9:
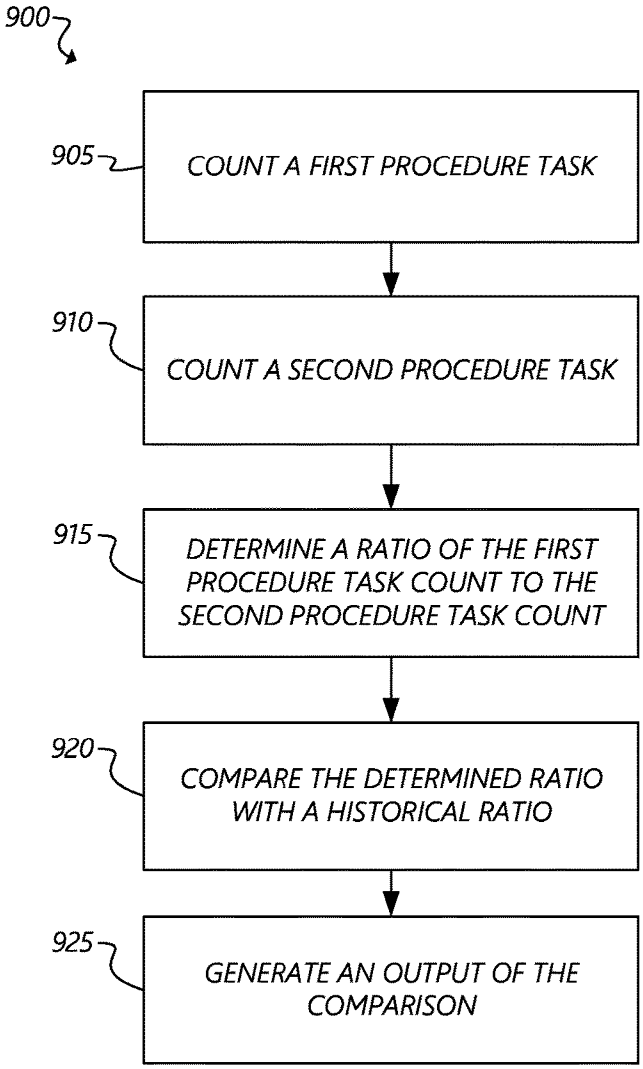
FIG. 9 is a flow diagram of a scoring process for medical tasks, according to certain embodiments.

FIG. 9 is a flow diagram of a scoring process 900 for medical tasks, according to certain embodiments. The scoring process 900 can be performed by the control system 140 or by another component of the medical system 100 of FIG. 1. While the following describes one possible sequence to the process, other embodiments can perform the process in a different order or may include additional steps or may exclude one or more of the steps described below.

At block 905, the control system 140 counts a number of times a first procedure task is performed. At block 910, the control system 140 counts a number of times a second procedure task is performed. At block 915, the control system 140 determines a ratio of the counted number for the first procedure task to the counted number for the second procedure task. At block 920, the control system 140 can compare the determined ratio with a historical ratio. For example, the historical ratio may be generated by analyzing historical records for the same procedure to determine a mean or median ratio.

In one example, during ureteroscopy basketing, the control system 140 can count a number of basket operations and count a number of ureteroscope retractions. The control system 140 can then determine a ratio of the number of basket operations to the number of ureteroscope retractions and compare the determined ratio with other ratios from previous ureteroscopy basketing procedures.

In one example for ureteroscopy driving, the control system 140 can count a number of times a user drives a scope manually and a number of times the user drives the scope robotically. Manual driving is generally used for surveying the kidney. Meanwhile, a scope is typically docked to the robotic system in order to perform basketing. The control system 140 can then determine a ratio of the number of times the user drives a scope manually to the number of times the user drives the scope robotically and compare the determined ratio with other recorded ratios from previous ureteroscopy procedures. This ratio can measure the level of adaptation of the user to robotic ureteroscopy.

In another example, during ureteroscopy lasing, the control system 140 can count a lasing time for a stone and determine a size and/or type of the stone. The control system 140 can then determine a ratio of the lasing time for the stone with the size of the stone and compare the determined ratio with previous ratios from other operations. By determining the type of the stone (e.g., uric acid, calcium oxalate monohydrate, struvite, cystine, brushite, etc.), the control system 140 can aggregate statics across surgical operations based on the type of the stone. For example, lasing duration and procedure duration can be broken out by type of stone.

At block 925, the control system 140 can generate an output of the comparison. Such an output can be a report, visual indicator, guide, score, graph, or the like. For example, the control system 140 may indicate that the user is performing at, below, or above a median or average value for the ratio in comparison to recorded ratios from previous operations. In some embodiments, the output may compare the current user with records of previous operations by that user to track the user's personal performance. In some embodiments, the output may compare the user with other medical professionals.

In one embodiment, the output can include a real-time indicator showing how the user's current performance compares to previous operations. Such an output can aid the user during surgery by, for example, giving the user input on how long to perform lasing based on the size of the stone. Other outputs can provide other relevant information for the user.

Various types of procedure tasks can be evaluated using the scoring process 900. For example, some ratios can include number of basket operations to number of ureteroscope retractions, number of times a user drives a scope manually to number of times the user drives the scope robotically, and lasing time for a stone to size of the stone.

Figure 10:
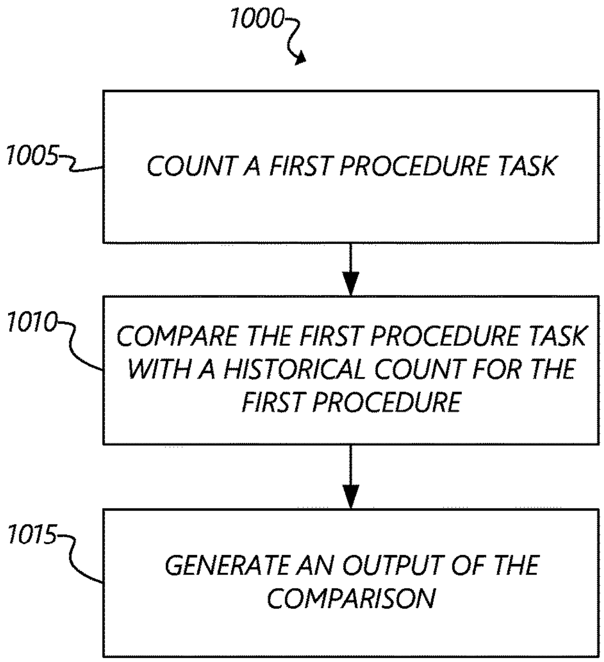
FIG. 10 is a flow diagram of another scoring process for medical tasks, according to certain embodiments.

FIG. 10 is a flow diagram of another scoring process for medical tasks, according to certain embodiments. The scoring process 1000 can be performed by the control system 140 or by another component of the medical system 100 of FIG. 1. While the following describes one possible sequence to the process, other embodiments can perform the process in a different order or may include additional steps or may exclude one or more of the steps described below.

At block 1005, the control system 140 can count a first procedure task. At block 1010, the control system 140 can compare the first procedure task with a historical count for the first procedure. For example, during ureteroscopy driving, the control system 140 may count the number of times a user attempts to insert a needle until the user succeeds and compares that count with the recorded needle insertion attempts from previous percutaneous needle insertion operations.

In another example, during percutaneous needle insertion, the control system 140 may count the time taken to survey a kidney before selecting a target calyx for percutaneous access and compare the counted time with recorded times from previous percutaneous needle insertion operations. The control system 140, during percutaneous needle insertion, may also count the number of times an automated alignment of the robotic manipulator with a catheter is initiated and compare the counted number of times with the recorded automated alignment numbers from previous operations.

During mini-PCNL alignment, the control system 140 may count a number of times an automated alignment of an end effector of the robotic manipulator with a catheter or sheath is initiated and compare the counted number of times with recorded automated alignment numbers from previous operations. In another example, the control system 140 during ureteroscopy lasing may count a number of times a view of the video capture device becomes occluded by dust from fragmentation of a stone and compare the counted number of times with recorded number of dust occlusions from previous operations.

At block 1015, the control system 140 can generate an output of the comparison. Such an output can be a report, visual indicator, guide, score, graph, or the like. For example, the control system 140 may indicate that the user is performing at, below, or above a median or average in comparison to recorded metrics from previous operations. In some embodiments, the output may compare the current user with records of previous operations by that user to track the user's personal performance. In some embodiments, the output may compare the user with other users.

In one embodiment, the output can include a real-time indicator showing how the user's current performance compares to previous operations. Such an output can aid the user during surgery by, for example, indicating whether the amount of dust from fragmentation is out of the ordinary. Other outputs can provide other relevant information for the user.

Various types of procedure tasks can be evaluated using the scoring process 1000. For example, some tasks can include: number of times a user attempts to insert a needle until the user successfully inserts the needle; counting time taken to survey a kidney before selecting a target calyx for percutaneous access; counting a number of times a navigational field generator for tracking a needle is repositioned; counting a number of times an automated alignment of the robotic manipulator with a catheter is initiated; and counting a number of times a view of the video capture device becomes occluded by dust from fragmentation of a stone.

Example Robotic System

Figure 11:
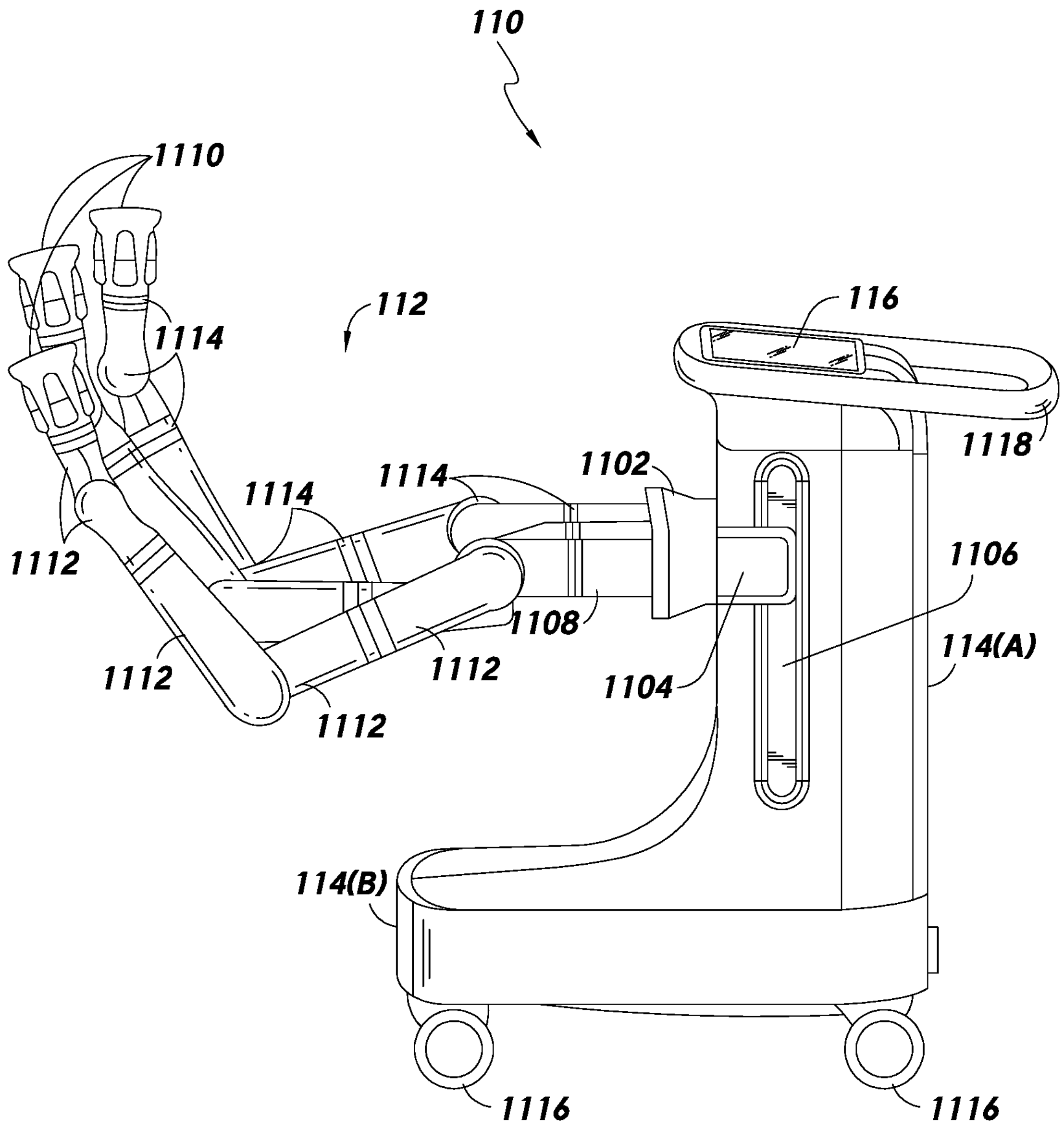
FIG. 11 illustrates example details of the robotic system, according to certain embodiments.

FIG. 11 illustrates example details of the robotic system 110 in accordance with one or more embodiments. In this example, the robotic system 110 is illustrated as a cart-based robotically-enabled system that is movable. However, the robotic system 110 can be implemented as a stationary system, integrated into a table, and so on.

The robotic system 110 can include the support structure 114 including an elongated section 114(A) (sometimes referred to as the "column 114(A)") and a base 114(B). The column 114(A) can include one or more carriages, such as a carriage 1102 (alternatively referred to as "the arm support 1102") for supporting the deployment of one or more the robotic arms 112 (three shown in the figure). The carriage 1102 can include individually configurable arm mounts that rotate along a perpendicular axis to adjust the base of the robotic arms 112 for positioning relative to a patient. The carriage 1102 can also include a carriage interface 1104 that allows the carriage 1102 to vertically translate along the column 114(A). The carriage interface 1104 is connected to the column 114(A) through slots, such as slot 1106, that are positioned on opposite sides of the column 114(A) to guide the vertical translation of the carriage 1102. The slot 1106 includes a vertical translation interface to position and hold the carriage 1102 at various vertical heights relative to the base 114(B). Vertical translation of the carriage 1102 allows the robotic system 110 to adjust the reach of the robotic arms 112 to meet a variety of table heights, patient sizes, physician preferences. etc. Similarly, the individually configurable arm mounts on the carriage 1102 allow a robotic arm base 1108 of the robotic arms 112 to be angled in a variety of configurations. The column 114(A) can internally comprise mechanisms, such as gears and/or motors, that are designed to use a vertically aligned lead screw to translate the carriage 1102 in a mechanized fashion in response to control signals generated in response to user inputs, such as inputs from the I/O device(s) 116.

In some embodiments, the slot 1106 can be supplemented with a slot cover(s) that is flush and/or parallel to the slot surface to prevent dirt and/or fluid ingress into the internal chambers of the column 114(A) and/or the vertical translation interface as the carriage 1102 vertically translates. The slot covers can be deployed through pairs of spring spools positioned near the vertical top and bottom of the slot 1106. The covers can be coiled within the spools until deployed to extend and retract from their coiled state as the carriage 1102 vertically translates up and down. The spring-loading of the spools can provide force to retract the cover into a spool when the carriage 1102 translates towards the spool, while also maintaining a tight seal when the carriage 1102 translates away from the spool. The covers can be connected to the carriage 1102 using, for example, brackets in the carriage interface 1104 to ensure proper extension and retraction of the covers as the carriage 1102 translates.

The base 114(B) can balance the weight of the column 114(A), the carriage 1102, and/or arms 112 over a surface, such as the floor. Accordingly, the base 114(B) can house heavier components, such as one or more electronics, motors, power supply, etc., as well as components that enable movement and/or immobilize the robotic system 110. For example, the base 114(B) can include rollable wheels 1116 (also referred to as "the casters 1116") that allow for the robotic system 110 to move around the room for a procedure. After reaching an appropriate position, the casters 1116 can be immobilized using wheel locks to hold the robotic system 110 in place during the procedure. As shown, the robotic system 110 also includes a handle 1118 to assist with maneuvering and/or stabilizing the robotic system 110.

The robotic arms 112 can generally comprise robotic arm bases 1108 and end effectors 1110, separated by a series of linkages 1112 that are connected by a series of joints 1114. Each joint 1114 can comprise an independent actuator and each actuator can comprise an independently controllable motor. Each independently controllable joint 1114 represents an independent degree of freedom available to the robotic arm 112. For example, each of the arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 1110 at a specific position, orientation, and/or trajectory in space using different linkage positions and/or joint angles. In some embodiments, the end effectors 1110 can be configured to engage with and/or control a medical instrument, a device, an object, and so on. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

As shown in FIG. 11, the robotic system 110 can also include the I/O device(s) 116. The I/O device(s) 116 can include a display, a touchscreen, a touchpad, a projector, a mouse, a keyboard, a microphone, a speaker, a controller, a camera (e.g., to receive gesture input), or another I/O device to receive input and/or provide output. The I/O device(s) 116 can be configured to receive touch, speech, gesture, or any other type of input. The I/O device(s) 116 can be positioned at the vertical end of column 114(A) (e.g., the top of the column 114(A)) and/or provide a user interface for receiving user input and/or for providing output. For example, the I/O device(s) 116 can include a touchscreen (e.g., a dual-purpose device) to receive input and provide a physician with pre-operative and/or intra-operative data. Example pre-operative data can include pre-operative plans, navigation, and/or mapping data derived from pre-operative computerized tomography (CT) scans, and/or notes from pre-operative patient interviews. Example intra-operative data can include optical information provided from a tool/instrument, sensor, and/or coordinate information from sensors, as well as vital patient statistics, such as respiration, heart rate, and/or pulse. The I/O device(s) 116 can be positioned and/or tilted to allow a physician to access the I/O device(s) 116 from a variety of positions, such as the side of the column 114(A) opposite the carriage 1102. From this position, the physician can view the I/O device(s) 116, the robotic arms 112, and/or a patient while operating the I/O device(s) 116 from behind the robotic system 110.

The robotic system 110 can include a variety of other components. For example, the robotic system 110 can include one or more control electronics/circuitry, power sources, pneumatics, optical sources, actuators (e.g., motors to move the robotic arms 112), memory, and/or communication interfaces (e.g. to communicate with another device). In some embodiments, the memory can store computer-executable instructions that, when executed by the control circuitry, cause the control circuitry to perform any of the operations discussed herein. For example, the memory can store computer-executable instructions that, when executed by the control circuitry, cause the control circuitry to receive input and/or a control signal regarding manipulation of the robotic arms 112 and, in response, control the robotic arms 112 to be positioned in a particular arrangement and/or to navigate a medical instrument connected to the end effectors 1110.

In some embodiments, robotic system 110 is configured to engage with and/or control a medical instrument, such as the basket retrieval device 120. For example, the robotic arms 112 can be configured to control a position, orientation, and/or tip articulation of a scope (e.g., a sheath and/or a leader of the scope). In some embodiments, the robotic arms 112 can be configured/configurable to manipulate the scope using elongate movement members. The elongate movement members can include one or more pull wires (e.g., pull or push wires), cables, fibers, and/or flexible shafts. To illustrate, the robotic arms 112 can be configured to actuate multiple pull wires coupled to the scope to deflect the tip of the scope. Pull wires can include any suitable or desirable materials, such as metallic and/or non-metallic materials such as stainless steel, Kevlar, tungsten, carbon fiber, and the like. In some embodiments, the scope is configured to exhibit nonlinear behavior in response to forces applied by the elongate movement members. The nonlinear behavior can be based on stiffness and compressibility of the scope, as well as variability in slack or stiffness between different elongate movement members.

Example Control System

Figure 12:
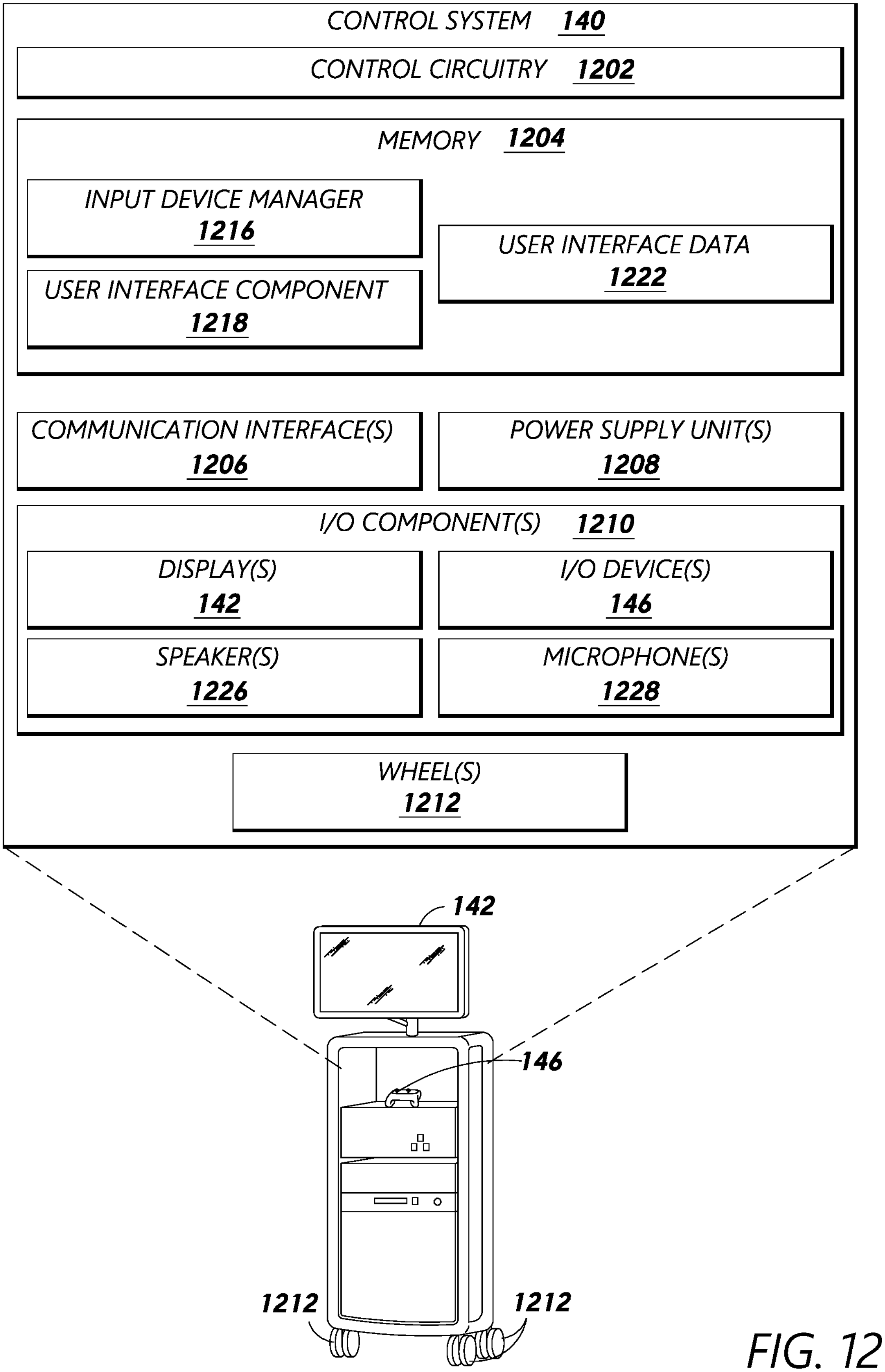
FIG. 12 illustrates example details of the control system, according to certain embodiments.

FIG. 12 illustrates example details of the control system 140 in accordance with one or more embodiments. As illustrated, the control system 140 can include one or more of the following components, devices, modules, and/or units (referred to herein as "components"), either separately/individually and/or in combination/collectively: control circuitry 1202, data storage/memory 1204, one or more communication interfaces 1206, one or more power supply units 1208, one or more I/O components 1210, and/or one or more wheels 1212 (e.g., casters or other types of wheels). In some embodiments, the control system 140 can comprise a housing/enclosure configured and/or dimensioned to house or contain at least part of one or more of the components of the control system 140. In this example, the control system 140 is illustrated as a cart-based system that is movable with the one or more wheels 1212. In some cases, after reaching the appropriate position, the one or more wheels 1212 can be immobilized using wheel locks to hold the control system 140 in place. However, the control system 140 can be implemented as a stationary system, integrated into another system/device, and so on.

Although certain components of the control system 140 are illustrated in FIG. 12, it should be understood that additional components not shown can be included in embodiments in accordance with the present disclosure. For example, graphical processing units (GPUs) or other specialized embedded chips may be included for running neural networks. Furthermore, certain of the illustrated components can be omitted in some embodiments. Although the control circuitry 1202 is illustrated as a separate component in the diagram of FIG. 12, it should be understood that any or all of the remaining components of the control system 140 can be embodied at least in part in the control circuitry 1202. That is, the control circuitry 1202 can include various devices (active and/or passive), semiconductor materials and/or areas, layers, regions, and/or portions thereof, conductors, leads, vias, connections, and/or the like, wherein one or more of the other components of the control system 140 and/or portion(s) thereof can be formed and/or embodied at least in part in/by such circuitry components/devices.

The various components of the control system 140 can be electrically and/or communicatively coupled using certain connectivity circuitry/devices/features, which can or may not be part of the control circuitry 1202. For example, the connectivity feature(s) can include one or more printed circuit boards configured to facilitate mounting and/or interconnectivity of at least some of the various components/circuitry of the control system 140. In some embodiments, two or more of the control circuitry 1202, the data storage/memory 1204, the communication interface(s) 1206, the power supply unit(s) 1208, and/or the input/output (I/O) component(s) 1210, can be electrically and/or communicatively coupled to each other.

As illustrated, the memory 1204 can include an input device manager 1216 and a user interface component 1218 configured to facilitate various functionality discussed herein. In some embodiments, the input device manager 1216, and/or the user interface component 1218 can include one or more instructions that are executable by the control circuitry 1202 to perform one or more operations. Although many embodiments are discussed in the context of the components 1216-1218 including one or more instructions that are executable by the control circuitry 1202, any of the components 1216-1218 can be implemented at least in part as one or more hardware logic components, such as one or more application specific integrated circuits (ASIC), one or more field-programmable gate arrays (FPGAs), one or more program-specific standard products (ASSPs), one or more complex programmable logic devices (CPLDs), and/or the like. Furthermore, although the components 1216-1218 are illustrated as being included within the control system 140, any of the components 1216-1218 can be implemented at least in part within another device/system, such as the robotic system 110, the table 150, or another device/system. Similarly, any of the other components of the control system 140 can be implemented at least in part within another device/system.

The input device manager 1216 can be configured to receive inputs from the input device 146 and translate them into actions performable by the robotic system 110. For example, pre-programmed motions, such as rapid open, rapid close, and jiggle motion, can be stored in the input device manager 1216. These pre-programmed motions can then be assigned to the desired input (e.g., single or dual button presses, voice commands, joystick movements, etc.). In some implementations, the pre-programmed motions are determined by the manufacturer. In other implementations, users may be able to modify existing pre-programmed motions and/or create new ones.

The user interface component 1218 can be configured to facilitate one or more user interfaces (also referred to as "one or more graphical user interfaces (GUI)"). For example, the user interface component 1218 can generate a configuration menu for assigning pre-programmed motions to inputs or a settings menu for enabling certain modes of operation or disabling selected pre-programmed motions in specific situations. The user interface component 1218 can also provide user interface data 1222 for display to the user.

The one or more communication interfaces 1206 can be configured to communicate with one or more device/sensors/systems. For example, the one or more communication interfaces 1206 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 1206 can implement a wireless technology such as Bluetooth, Wi-Fi, near field communication (NFC), or the like.

The one or more power supply units 1208 can be configured to manage power for the control system 140 (and/or the robotic system 110, in some cases). In some embodiments, the one or more power supply units 1208 include one or more batteries, such as a lithium-based battery, a lead-acid battery, an alkaline battery, and/or another type of battery. That is, the one or more power supply units 1208 can comprise one or more devices and/or circuitry configured to provide a source of power and/or provide power management functionality. Moreover, in some embodiments the one or more power supply units 1208 include a mains power connector that is configured to couple to an alternating current (AC) or direct current (DC) mains power source.

The one or more I/O components 1210 can include a variety of components to receive input and/or provide output, such as to interface with a user. The one or more I/O components 1210 can be configured to receive touch, speech, gesture, or any other type of input. In examples, the one or more I/O components 1210 can be used to provide input regarding control of a device/system, such as to control the robotic system 110, navigate the scope or other medical instrument attached to the robotic system 110, control the table 150, control the fluoroscopy device 190, and so on. As shown, the one or more I/O components 1210 can include the one or more displays 142 (sometimes referred to as "the one or more display devices 142") configured to display data. The one or more displays 142 can include one or more liquid-crystal displays (LCD), light-emitting diode (LED) displays, organic LED displays, plasma displays, electronic paper displays, and/or any other type(s) of technology. In some embodiments, the one or more displays 142 include one or more touchscreens configured to receive input and/or display data. Further, the one or more I/O components 1210 can include the one or more input devices 146, which can include a touchscreen, touch pad, controller, mouse, keyboard, wearable device (e.g., optical head-mounted display), virtual or augmented reality device (e.g., head-mounted display), etc. Additionally, the one or more I/O components 1210 can include one or more speakers 1226 configured to output sounds based on audio signals and/or one or more microphones 1228 configured to receive sounds and generate audio signals. In some embodiments, the one or more I/O components 1210 include or are implemented as a console.

Although not shown in FIG. 9, the control system 140 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). Further, the control system 140 can include a voltage and/or surge protector designed to provide filtered and/or protected electrical power to another device, such as the robotic system 110, thereby avoiding placement of a power transformer and other auxiliary power components in the robotic system 110, resulting in a smaller, more moveable robotic system 110.

The control system 140 can also include support equipment for sensors deployed throughout the medical system 100. For example, the control system 140 can include opto-electronics equipment for detecting, receiving, and/or processing data received from optical sensors and/or cameras. Such opto-electronics equipment can be used to generate real-time images for display in any number of devices/systems, including in the control system 140.

In some embodiments, the control system 140 can be coupled to the robotic system 110, the table 150, and/or a medical instrument, such as the scope and/or the basket retrieval device 120, through one or more cables or connections (not shown). In some implementations, support functionality from the control system 140 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A robotic system for automatically identifying phases of a medical procedure, the robotic system comprising:
- a video capture device;
- a robotic manipulator;
- one or more sensors configured to produce sensor data indicating a position of the robotic manipulator;
- an input device configured to receive one or more user inputs; and
- control circuitry communicatively coupled to the robotic manipulator, the control circuitry configured to:
  - receive sensor data from the one or more sensors;
  - determine that the robotic manipulator is in a first position based on the sensor data from the one or more sensors;
  - determine a set of procedure phases associated with the first-medical procedure;
  - identify a subset of procedure phases within the set of procedure phases based on at least one of the first position of the robotic manipulator or a user input;
  - perform a first analysis of a video captured by the video capture device based on a machine learning algorithm configured to identify one or more features of the video;
  - identify a phase of the medical procedure from the subset of procedure phases based at least in part on the one or more features of the video identified by the machine learning algorithm; and
  - annotate the video with a first video marker indicating a beginning of the first associated with the identified phase of the medical procedure.

2. The robotic system of claim 1, the control circuitry further configured to:
- determine that the medical procedure is a first procedure from a set of procedures based on at least one of a second user input or the sensor data from the one or more sensors, wherein the set of procedures comprises at least ureteroscopy, percutaneous nephrolithotomy (PCNL), and mini-PCNL.

3. The robotic system of claim 1, wherein the sensor data comprises radio-frequency identification (RFID) data of one or more medical instruments utilized by the robotic manipulator.

4. The robotic system of claim 1, further comprising:

a user interface (UI) including a plurality of UI screens associated with a set of procedures, wherein the one or more user inputs include a selection of a UI screen, of the plurality of UI screens, associated with the medical procedure.

5. The robotic system of claim 1, wherein the first video marker indicates a beginning of the identified phase of the medical procedure, the control circuitry further configured to:

determine that the robotic manipulator is in a second position based on the sensor data from the one or more sensors; and annotate the video with a second video marker indicating an ending of the identified phase of the medical procedure based at least in part on the second position of the robotic manipulator and video captured by the video capture device while the robotic manipulator is in the second position.

6. The robotic system of claim 1, wherein the robotic manipulator is configured to manipulate a medical instrument comprising a ureteroscope.

7. The robotic system of claim 1, wherein the video is annotated with a plurality of video markers associated with different phases of the medical procedure, the plurality of video markers including the first video marker.

8. The robotic system of claim 1, the control circuitry further configured to:

in response to identifying the phase of the medical procedure, triggering automated movement of the robotic manipulator to a second position.

9. The robotic system of claim 8, wherein the automated movement of the robotic manipulator to the second position comprises:

moving a medical instrument to an insertion site; and aligning the medical instrument along a pre-determined insertion trajectory into the insertion site.

10. The robotic system of claim 1, the control circuitry further configured to:

determine whether a medical instrument is at a target location associated with the identified phase of the medical procedure; and in response to determining that the medical instrument is at the target location, indicate success of the identified phase of the medical procedure on a user interface of the robotic system.

11. The robotic system of claim 10, the control circuitry further configured to:

determine a success rate for the identified phase of the medical procedure based on whether the medical instrument is at the target location during the identified phase across multiple instances of the medical procedure.

12. The robotic system of claim 1, the control circuitry further configured to:

associate results of the identified phase with a user of the robotic system.

13. The robotic system of claim 1, further comprising:

a sensor for determining a location of a medical instrument manipulated by the robotic manipulator.

14. A method for automatically identifying phases of a medical procedure using a robotic system comprising a video capture device, a robotic manipulator, one or more sensors, and an input device, the method comprising:

receiving sensor data from the one or more sensors;

determining that the robotic manipulator is in a first position based on the sensor data from the one or more sensors;

determining a set of procedure phases associated with the medical procedure;

identifying a subset of procedure phases within the set of procedure phases based on at least one of the first position of the robotic manipulator or a user input;

performing a first analysis of a video captured by the video capture device based on a machine learning algorithm configured to identify one or more features of the video;

identifying a phase of the medical procedure from the set subset of procedure phases based at least in part on the one or more features of the video identified by the machine learning algorithm; and annotating the video with a first video marker associated with the identified phase of the medical procedure.

15. The method of claim 14, further comprising:

determining that the robotic manipulator is in a second position based on the sensor data from the one or more sensors; and annotating the video with a second video marker indicating an ending of the identified phase of the medical procedure based at least in part on the second position of the robotic manipulator and video captured by the video capture device while the robotic manipulator is in the second position.

16. The method of claim 14, further comprising:

determining that the medical procedure is a first procedure from a set of procedures based on at least one of a second user input or the sensor data from the one or more sensors, wherein the first procedure is a ureteroscopy and the identified phase comprises a surveying phase, a second phase comprises a lasing phase, and a third phase comprises a basketing phase.

17. The method of claim 14, further comprising:

annotating the video with a plurality of video markers associated with different phases of the medical procedure, the plurality of video markers including the first video marker.

18. The method of claim 14, further comprising:

in response to identifying the phase of the medical procedure, triggering automated movement of the robotic manipulator to a second position.

19. The method of claim 18, wherein the automated movement of the robotic manipulator to the second position comprises:

moving a medical instrument to an insertion site; and aligning the medical instrument along a pre-determined insertion trajectory.

20. A control system for automatically identifying phases of a medical procedure performed by a robotic device, the control system comprising:

a communication interface configured to receive sensor data indicating a position of a robotic device, user input data, and video data captured by a video capture device;

memory configured to store the sensor data and the video data; and one or more processors configured to:

determine that the robotic device is in a first position based on the sensor data from the one or more sensors;

determine a set of procedure phases associated with the medical procedure;

identify a subset of procedure phases within the set of procedure phases based on at least one of the first position of a robotic manipulator or a user input;

perform an analysis of a video captured by a video capture device based on a machine learning algorithm configured to identify one or more features of the video;

identify a phase of the medical procedure from the subset of procedure phases based at least in part on the one or more features of the video identified by the machine learning algorithm; and annotate the video with a first video marker associated with the identified phase of the medical procedure.

* * * * *